(12) United States Patent
Shapiro

(10) Patent No.: US 6,746,678 B1
(45) Date of Patent: *Jun. 8, 2004

(54) METHOD OF TREATING NEUROLOGICAL DISEASES AND ETIOLOGICALLY RELATED SYMPTOMOLOGY USING CARBONYL TRAPPING AGENTS IN COMBINATION WITH MEDICAMENTS

(76) Inventor: Howard K. Shapiro, 214 Price Ave., Apt. F-32, Narberth, PA (US) 19072

( * ) Notice: Subject to any disclaimer, the term of this patent is extended or adjusted under 35 U.S.C. 154(b) by 0 days.

This patent is subject to a terminal disclaimer.

(21) Appl. No.: 09/545,870

(22) Filed: Apr. 6, 2000

Related U.S. Application Data

(63) Continuation-in-part of application No. 08/883,290, filed on Jun. 26, 1997, now abandoned, which is a continuation-in-part of application No. 08/062,201, filed on Jun. 29, 1993, now Pat. No. 5,668,117, which is a continuation-in-part of application No. 08/026,617, filed on Feb. 23, 1993, now abandoned, which is a continuation of application No. 07/660,561, filed on Feb. 22, 1991, now abandoned.

(51) Int. Cl.[7] .............................. A61K 9/00; A61K 9/20; A61K 6/48; A01N 37/44
(52) U.S. Cl. ...................... 424/400; 424/464; 424/451; 514/565; 514/561; 514/567
(58) Field of Search ................ 424/78.08, 464, 424/451, 400; 514/150, 565, 561, 567

(56) References Cited

U.S. PATENT DOCUMENTS

| | | | | |
|---|---|---|---|---|
| 5,283,068 A | * | 2/1994 | Koch | 424/679 |
| 5,358,720 A | * | 10/1994 | Koppel et al. | 424/639 |
| 5,405,613 A | * | 4/1995 | Rowland | 424/439 |
| 5,532,275 A | * | 7/1996 | Grumet | 514/567 |
| 5,668,117 A | * | 9/1997 | Shapiro | 514/55 |

OTHER PUBLICATIONS

52nd eddition, Physician Desk Reference, 1998, p. 1184.*

* cited by examiner

Primary Examiner—Thurman K. Page
Assistant Examiner—Blessing Fubara

(57) ABSTRACT

This invention defines a novel method for treatment of several neurological diseases and pathophysiologically related symptomology, said diseases including peripheral neuropathies, secondary symptomology of diabetes, Alzheimer's disease, Parkinson's disease, alcoholic polyneuropathy and age-onset symptomology, as well as analogous veterinary disease states. An opportunity exists for pharmacological intervention in some neurological diseases by use of water soluble, small molecular weight primary amine agents and chemical derivatives thereof. Examples of such primary pharmacological agents include 4-aminobenzoic acid and derivatives thereof. The present invention also includes: (1) oral use of optional non-absorbable polyamine polymeric co-agents such as chitosan, (2) oral use of optional known antioxidant co-agents and nutritional factors related thereto, and (3) use of the primary agents and co-agents noted above in optional combination with medicaments recognized as effective for treatment of the diseases addressed herein or symptoms thereof.

33 Claims, No Drawings

METHOD OF TREATING NEUROLOGICAL DISEASES AND ETIOLOGICALLY RELATED SYMPTOMOLOGY USING CARBONYL TRAPPING AGENTS IN COMBINATION WITH MEDICAMENTS

RELATED PATENT APPLICATIONS

This invention is a continuation-in-part of U.S. patent application Ser. No. 08/883,290, filed on Jun. 26, 1997entitled "Methods of Treating Neurological Diseases and Etiologically Related Symptomology Using Carbonyl Trapping Agents in Combination with Medicaments," now abandoned, which in turn is a continuation-in-part of patent application Ser. No. 08/062,201, filed on Jun. 29, 1993 now U.S. Pat. No. 5,668,117 entitled "Method of Treating Neurological Diseases and Etiologically Related Symptomology Using Carbonyl Trapping Agents in Combination with Previously Known Medicaments," which in turn is a continuation-in-part of U.S. patent application Ser. No. 08/026,617, filed on Feb. 23, 1993 entitled "Method of Treating Neurological Diseases and Etiologically Related Symptomology Using Carbonyl Trapping Agents," now abandoned, which in turn is a continuation of U.S. patent application Ser. No. 07/660,561, filed on Feb. 22, 1991 entitled "Method of Treating Neurological Diseases and Etiologically Related Symptomology Using Carbonyl Trapping Agents," now abandoned, the entire disclosures of which are incorporated by reference herein.

BACKGROUND OF THE INVENTION

1. Field of the Invention

This invention relates to the clinical treatment of neurodegenerative diseases. For purposes of this invention, the category of neurodegenerative diseases includes hereditary motor and sensory neuropathies (HMSN, also known as peroneal muscular atrophy or Charcot-Marie-Tooth disease), diabetic polyneuropathy, Alzheimer's pre-senile and senile dementia, Down's syndrome, Parkinson's disease, olivopontocerebellar atrophy, Huntington's disease, amyotrophic lateral sclerosis, age-onset neurological deterioration, alcoholic polyneuropathy, tinnitus, multiple sclerosis, and pathophysiologically symptomology.

The clinical neurology literature includes many descriptions of patients having an incipient form of a disease, patients showing the recognized symptoms of a disease and additional symptomology, and patients demonstrating concurrent clinical symptomology of two or more of the disease entities included in the category of neurodegenerative diseases defined above. Such clinical disorders are frequently excluded from biochemical studies due to inherent problems of classification and their happenstance occurrence. Hence comparatively little research information is available on such clinical phenomena. Yet it is the understanding of this inventor that information available on the etiologies of well recognized neurological disorders, as summarized herein, can also be extrapolated to infer that the drug therapies described in this invention may also be applied with success to the incipient and more complex forms of the diseases mentioned above. Furthermore, many genetic sub-categories of these neurodegenerative diseases are now recognized in the prior art. For purposes of this invention, the term "pathophysiologically symptomology" shall include those various clinical and genetic sub-categories of the class of neurodegenerative diseases noted above as commonly recognized in the prior art.

2. Description of Prior Art

The logic and potential value, even synergistic value, of using two or more therapeutic agents in combination has been recognized previously [Ghose et al. Int. *J. Radiat. Biol.* 44:175–181 (1983); Goldstein et al. *Adv. Neurol.* 53:101–106 (1990); Rinne *Acta. Neurol Scand.* 84[Suppl. 136]:95–98 (1991)]. For example, in a study on two-drug combinations of memory enhancing agents Flood and coworkers [*Life Sci.* 42:2145–2154 (1988)] noted that:

> The potential for clinically desirable drug interactions has been emphasized for drugs in general (1) and for memory enhancing drugs in particular (2,3). For example, individual cholinergic drugs which improve memory retention test scores (4,5,6) do so in two-drug combinations at substantially lower doses than would be predicted if the two drugs acted additively (7,8,9) . . .
>
> In prior studies of the effect of two-drug combinations on memory processing (8,9), we determined the effect of varying the dose of two drugs while holding the ratio constant. The ratio was based on the optimal memory enhancing doses of each drug administered singly. These studies showed that drugs administered in certain combinations require 67 to 96% less drug to improve retention, than when the same drugs were administered alone. This type of drug interaction was said to yield supra-additivity.

The present disclosure describes the inventive concept of using the therapeutic technology of U.S. patent application Ser. No. 08/026,617 in combination with pharmaceutical agents recognized as having, or possibly having some medicinal value for treatment of the disease entities noted above. No pharmacological treatment of comprehensive effectiveness is currently available for any of the neurological disorders discussed herein. However, a variety of pharmaceutical agents have been described which may offer at least some degree of symptomatic relief from the clinical effects of these diseases.

The use of L-dopa as the primary therapeutic agent for treatment of Parkinson's disease may serve as an example of the limitations of present technology. Citing earlier work, Robin [*Am. J. Med. Sci.* 301:277–280 (1991)] has noted that " . . . chronic exposure to high dose L-dopa may accelerate the progression of Parkinson's disease." Indeed, clinical benefits to be obtained from L-dopa therapy are predictably limited to perhaps three to five years. After that period, continued use of L-dopa will not provide clinical benefit. This situation exists because L-dopa therapy depends on conversion of this physiological precursor into dopamine within a population of substantia nigra neurons which is selectively deteriorating in this disease. Once the last of these nerve cells is gone, the therapeutic strategy has lost its physiological basis.

As noted by Ceballos and coworkers [in *Antioxidants in Therapy and Preventive Medicine*, Emerit, I, sr. ed. (New York, Plenum Press, 1990) pp. 493–498]:

> . . . The development of clinical features in AD [Alzheimer's disease] is linked to the amount of deposition of amyloid in the limbic areas and cerebral cortex. Moreover, amyloid formation may arise as a consequence of membrane damage . . . due to lipid peroxidation . . . About 6% of PHF [paired helical filaments] is composed of the amino-acid, hydroxyproline. This amino-acid is not a constituent of cytoplasmic protein in normal brain and the abundance of hydroxyproline in cytoplasmic PHF involves non-enzymatic hydroxylation of proline residues probably by hydroxyl free radicals. This free radical hypothesis of PHF formation suggests that AD is an acceleration of the normal aging process in affected brain regions.

Some published work has reported that L-deprenyl (selegiline) may work in part by slowing the aging process [Sanchez-Ramos *Clin. Neuropharmocol.* 14:391–402 (1991)]. Monoamine oxidase B (MAO-B) activity, which is thought to increase with aging in some areas of the brain, generates $H_2O_2$, which in turn may generate neurocytotoxic hydroxyl free radicals (HO$^-$) and leads to subsequent lipid peroxidation. Hence, use of MAO-B inhibitors such as L-deprenyl may have an anti-aging clinical effect [Youdim *Adv. Neurol.* 53:483–488 (1990)]. The use of L-deprenyl as a clinical agent for treatment of canine age-related dementia is an example of the potential veterinary applications of the prior art drugs included in this invention [Milgram U.S. Pat. No. 5,151,449 (Sep. 29, 1992)].

As discussed in U.S. patent application Ser. No. 08/026,617, a considerable body of prior art publications has provided evidence suggesting that the etiologies of certain neurodegenerative diseases include evidence of chemical crosslinking of neurofilaments. Such studies include work on hereditary motor and sensory neuropathies [Hughes and Brownell *J. Neurol. Neurosurg. Psych.* 35:648–657 (1972); Brimijoin et al. *Science* 180:1295–1297 (1973); van Weerden et al. *Muscle & Nerve* 5:185–196 (1982); Goebel et al. *Ital. J. Neurol. Sci.* 7:325–332 (1986)], giant axon neuropathy [Prineas et al. *J. Neuropathol. Exp. Neurol.* 35:458–470 (1976)], diabetic polyneuropathy [Yamamura et al. in *Diabetic Neuropathy*, Goto, Y, sr. ed. (Princeton, Excerpta Medica, 1982) pp. 80–85; Sidenius and Jakobsen *Diabetes* 31:689–693 (1982); Tomlinson and Mayer *J. Auton. Pharmac.* 4:59–72 (1984)], Alzheimer's disease [Wisniewski et al. *J. Neuropath. Exp. Neurol.* 29:163–176 (1970); Iqbal et al. *Brain Res.* 142:321–332 (1978); Wisniewski et al. in *Aging and Cell Structure*, volume 1, Johnson, Jr., J E, ed. (New York, Plenum Press, 1982) pp. 110–112], Down's syndrome [Goodison et al. *Soc. Neurosci. Abstr.* 15(pt. 2): 329 (abstract 135.6) (1989)], Pick's disease [Yoshimura *Clin. Neuropath.* 8:1–6 (1989)], Parkinson's disease [Oppenheimer in *Greenfield's Neuropathology*, Blackwood, W and Corsellis, JAN, eds. (Chicago, Year Book Medical Publishers, 1976) pp. 612–614; Cohan in *Clinical Aspects of Aging*, third edition, Reichel, W, ed. (Baltimore, Williams & Wilkens, 1989) pg. 167], amyotrophic lateral sclerosis [Carpenter *Neurology* 18:841–851 (1968)], infantile spinal muscular atrophy [Lee et al. *Neuropediatrics* 20:107–111 (1989)], Friedreich's ataxia [Lamarche et al. *Can. J. Neurol. Sci.* 9:137–139 (1982)] and alcoholic polyneuropathy [Appenzeller and Richardson *Neurology* (Minneap) 16:1205–1209 (1966)]. For the purposes of the present disclosure, neurofilaments present in the nerve cells of the central nervous system, autonomic nervous system and peripheral nervous system are, as a class, defined as an example of the nerve cell structures that may reasonably be expected to be protected by use of the compositions of the present invention.

Likewise, evidence of increased deposition of lipofuscin in various neurodegenerative diseases has been presented. This observation has been documented in studies on amyotrophic lateral sclerosis [Carpenter *Neurology* 18:841–851 (1968)], Guam Parkinsonism-dementia [Tan et al. *Clin. Exp. Neurol.* 17:227–234 (1981)], Alzheimer's disease [Tsuchida et al. *Chem. Phys. Lipids* 44:297–325 (1987); Moran and Gomez-Ramos *Soc. Neurosci. Abstr.* 15(pt. 2):1039 (abstract 414.8) (1989)], Huntington's disease [Tellez-Nagel et al. *J. Neuropathol. Exp. Neurol.* 33:308–332 (1974)], Meniere's disease [Ylikoski *Arch. Otolaryngol.* 106:477–483 (1980)], and juvenile ceroid-lipofuscinosis [Schwendemann in *Ceroid-Lipofuscinosis* (*Batten Disease*), Armstrong, D, sr. ed. (New York, Elsevier Biomedical Press, 1982) pp. 117–136]. Heart lipofuscin has been shown to have the following general composition: lipids, 20–50%; protein, 30–60%; and strongly pigmented resin-like hydrolysis-resistant material, 9–20%. Although the exact nature of the hydrolysis-resistant chemical bonds remains to be unequivically defined, the similarity between lipofuscin fluorescence and that of Schiff bases formed between malondialdehyde and primary amines suggests that similar chemical crosslinks may be part of lipofuscin structure [Tsuchida et al. *Chem. Phys. Lipids* 44:297–325 (1987)].

The results of several published research studies suggest that dysfunctional lipid peroxidation may be a contributing factor in the etiology of Parkinson's disease [Fahn *Ann. NY Acad. Sci.* 570:186–196 (1989)], multiple sclerosis [Hunter *Neurochem. Res.* 10:1645–1652 (1985)] and Duchenne muscular dystrophy [Kar and Pearson *Clin. Chim. Acta* 94:277–280 (1979); Jackson et al. *Med. Biol.* 62:135–138 (1984); Hunter and Mohamed *Clin. Chim.Acta* 155:123–132 (1986)].

For the purposes of the present disclosure, evidence of increased deposition of lipofuscin present in the nerve cells of the central nervous system, autonomic nervous system and peripheral nervous system is defined as an example of the nerve cell deterioration that may reasonably be expected to be ameliorated by use of the compositions of the present invention.

Age-related changes share much in common with other disease entities discussed in this invention. At the biochemical level, the two most clearly defined pathological events within aging mammalian cells appear to be (1) the progressive accumulation of lipofuscin and (2) concomitant appearance of high molecular weight protein aggregates and/or polymeric lipid-protein complexes [Shimasaki et al. *Biochim. BioPhys. Acta* 792:123–129 (1984)]. Age-onset peripheral nerve damage has been recognized in both man and experimental animals. Such polyneuropathy is extremely common in the elderly [Cohan in *Clinical Aspects of Aging*, third edition, Reichel, W, ed. (Baltimore, Williams & Wilkens, 1989) pp. 163–176]. Examination of human sural nerve biopsies has revealed age-related degeneration of both myelinated and non-myelinated fibers. This process includes the occurrence of unusual inclusions within axons consisting of filament bundles which appear more dense than those of normal neurofilaments [Ochoa and Mair *Acta Neuropath.* (Berl.) 13:217–239 (1969)]. As peripheral, autonomic and central nervous system neurons lose functional ability as part of the aging process a variety of body functions under their control are adversely affected.

Autonomic nervous system functions include urinary continence, peristaltic movement of the digestive tract, sexual response and breathing. Forms of neurological dysfunction lying within the scope of this invention which may cause urinary incontinence include: Alzheimer's senile dementia, demyelinating diseases such as multiple sclerosis, peripheral nerve lesions, diabetes mellitus and alcoholic polyneuropathy [Palmer *Urinary Incontinence* (Thorofare, N.J., Slack Publishing, 1985) pg. 27]. Causes of urinary incontinence which may be classified as urological/gynecological, psychological or environmental [Palmer *Urinary Incontinence* (Thorofare, N.J., Slack Publishing, 1985) pg. 22] do not fall within the scope of this invention. Peristaltic movement of the digestive tract may be adversely affected due to aging, diabetes [Bergmann et al. *Eur. J. Clin. Pharmacol.* 43:121–124 (1992)] or other clinical disorders.

In their study on human senile and diabetic cataracts, Rao and Cotlier [*Invest. Ophthalmol. Vis. Sci.* 27:98–102 (1986)] noted evidence that crosslinking of lens proteins via non-enzymatic glycosylation appears to be an underlying pathological mechanism for both cataract types. In their analysis of senile cataracts these investigators observed statistically significant decreases in soluble protein content, increases in insoluble proteins, decreases in free ε-amino groups of insoluble proteins and increases in observed 5-hydroxymethyl furfural levels (that is, reducible Maillard products) in insoluble proteins. Similar data were obtained from diabetic cataracts. Earlier studies showed the appearance of covalently crosslinked protein polymers during senile cataract formation [Selkoe et al. *Science* 215:1243–1245 (1982)]. Evidence of increased lipid peroxidation in the aged human lens has also been presented [Bhuyan et al. *Life Sci.* 38:1463–1471 (1986)].

In addition, several published studies have presented evidence which implicates lipid peroxidation products in the etiology of atherosclerosis [Halliwell *Drugs* 42:569–605 (1991)]. 4-Hydroxy-2,3-trans-nonenal covalently binds to lysine and other peptide residues of low-density lipoprotein much more readily than malondialdehyde. Hence, it (as well as other aldehydes) may play a role in the etiology of atherosclerotic lesions [Jurgens et al. *Biochim. Biophys. Acta* 875:103–114 (1986); Esterbauer et al. *J. Lipid Res.* 28:495–509 (1987)]. As summarized by Steinbrecher [*J. Biol. Chem.* 262:3603–3608 (1987)], there is reason to believe that reactive lipid peroxidation agents form Schiff base adducts with the lysine ε-amino groups of low density lipoproteins (LDL). Such modified LDL's are recognized by high-affinity acetyl-LDL receptors located on macrophages, which results in lipid accumulation. Lipid-laden macrophages appear to be precursors of the foam cells which populate early atherosclerotic lesions [Steinbrecher *J. Biol. Chem.* 262:3603–3608 (1987)]. Use of the invention of U.S. patent application Ser. No. 08/026,617 in combination with effective medicaments for treatment of atherosclerosis, hypertension and ischemic heart disease, as defined herein, may provide additional clinical benefit for patients suffering from these chronic, age-related diseases. On these grounds, atherosclerosis, hypertension and ischemic heart disease are further included in the term "pathophysiologically symptomology" as defined herein.

For the purposes of the present disclosure, evidence of increased lipid peroxidation present in the nerve cells of the central nervous system, autonomic nervous system and peripheral nervous system is defined as yet another example of the nerve cell deterioration that may reasonably be expected to be ameliorated by use of the compositions of the present invention.

This inventor has published the findings of a study which may describe part of the physiological basis of one of the hereditary motor and sensory neuropathies [Shapiro et al. *Muscle & Nerve* 9(suppl. 5S):128 (1986); Shapiro and Kahn in *Charcot-Marie-Tooth Disorders: Pathophysiology, Molecular Genetics, and Therapy*, Lovelace, R E and Shapiro, H K, eds. (New York, Wiley-Liss, 1990) pp. 365–371]. In this study urine samples from five autosomal dominant chromosome 17 HMSN patients of the same family and five urine samples from age- and sex-matched normal control subjects were examined. By use of gas chromatography/mass spectrometry the urine concentrations of approximately 150 organic acids could be estimated in each sample. Average HMSN organic acid values differed most notably from normal values in a set of three physiologically related metabolites, 5-hydroxymethyl-2-furoic acid, 2,5-furandicarboxylic acid and 5-carboxy-2-furoylglycine. Average patient urine concentrations of these three organic acids were 29%, 50% and 37% of controls, respectively.

5-Carboxy-2-furoylglycine is a mono-glycine conjugate of 2,5-furandicarboxylic acid. Hence 2,5-furandicarboxylic acid was measured directly as the dicarboxylic acid and indirectly as its monoglycine conjugate. Glycine conjugation is a well recognized liver detoxication/excretion reaction, applied broadly to the

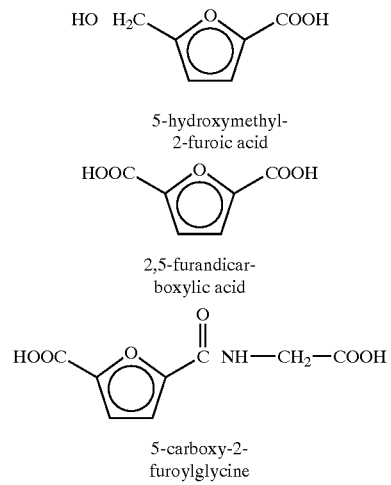

5-hydroxymethyl-
2-furoic acid 2,5-furandicar-
boxylic acid 5-carboxy-2-
furoylglycine carboxylic acid products of many endogenous metabolites, dietary components and drugs [Williams *Detoxication Mechanisms: The Metabolism and Detoxication of Drugs, Toxic Substances and Other Organic Compounds* (New York, John Wiley & Sons, 1959) pp. 349–353)].

Previous research studies have determined that 5-hydroxymethyl-2-furoic acid and 2,5-furandicarboxylic acid are oxidation products of an aldehyde precursor, 5-hydroxymethyl-2-furfural [Jellum et al. *Clin. Chim. Acta* 47:191–201 (1973)]. Decreased levels of furancarboxylic acid excretion suggest that this metabolite, and possibly other aldehyde precursors such as 2,5-furandialdehyde, is not being detoxicated and cleared in a normal manner. Several enzymes may be involved in the normal detoxication of furanaldehydes. Oxidation of furanaldehydes to carboxylic acid products is known to occur in mammalian tissues [Williams *Detoxication Mechanisms: The Metabolism and Detoxication of Drugs, Toxic Substances and Other Organic Compounds* (New York, John Wiley & Sons, 1959) pp. 550–551], but a specific furanaldehyde dehydrogenase has not been characterized.

Prior art studies have demonstrated the existance of several mammalian aldehyde dehydrogenases which possess wide substrate specificities [Hjelle and Petersen *Pharmacol. Biochem. Behav.* 18:155–160 (1983); Lindahl and Evces *Biochem. Pharmacol.* 33:3383–3389 (1984)]. These are NAD(P)-dependent enzymes. Normal detoxication of furanaldehydes may involve roles for one or more of these enzymes, or their flavin-dependent counterpart, and the HMSN patients studied by this inventor and coworkers may have a genetic defect in this process.

5-Hydroxymethyl-2-furfural should be regarded as a potential protein crosslinking agent [Jellum et al. *Clin. Chim. Acta* 47:191–201 (1973)]. 2,5-Furandialdehyde is even more suspect as a potential crosslinking agent, as it bears two highly reactive aldehyde groups. It is a close structural analogue of 2,5-hexanedione, a potent chemical peripheral neurotoxin implicated in the covalent crosslinking of neurofilaments.

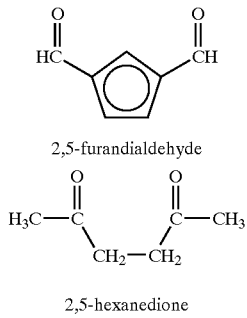

2,5-furandialdehyde 2,5-hexanedione

Hence 2,5-furandialdehyde appears to be a particularly interesting metabolite. It is cleared from the body only with difficulty in patients having a genetic peripheral neuropathy; and its size, three dimensional shape and analogous bi-carbonyl structure make it structurally related to a chemical known to induce peripheral neuropathy in mammals after relatively trace levels of exposure [Krasavage et al. *Toxicol. Appl. Pharmacol.* 52:433–441 (1980)]. Covalent chemical crosslinking of neurofilaments has been shown to be the basis of 2,5-hexanedione neurotoxicity [Carden et al. *Neurochem. Pathol.* 5:25–35 (1986)].

There is reason to believe that 5-hydroxymethyl-2-furfural and 2,5-furandialdehyde can originate as by-products of either of two general areas of metabolism, that of sugars and lipids. The thought that secondary products of lipid peroxidation might include metabolites such as 5-hydroxymethyl-furanaldehyde and 2,5-furandialdehyde has attracted little, if any, attention within the biomedical research community prior to submission of U.S. patent application Ser. No. 07/660,561. As described in that disclosure, 2,5-dimethyl furan appears to be a key intermediate in the process leading to the appearance of these aldehydes.

5-Hydroxymethyl-2-furfural and 2,5-furandialdehyde can also form spontaneously from glucose or fructose under mildly acidic aqueous conditions and, as they are readily generated during food cooking, they are part of the human diet. There is reason to believe that these aldehydes, among others, may play a significant role in the etiology of diabetic polyneuropathy. As discussed in U.S. patent application Ser. No. 08/026,617, it is the understanding of this inventor that conversion of fructose to 5-hydroxymethyl furfural and possibly 2,5-furandialdehyde may in fact be the basis of neurotoxic consequences resulting from activation of the polyol pathway seen in diabetic polyneuropathy.

Studies during the past decade have clearly established that long-term hyperglycemia associated with diabetes leads to generalized non-enzymatic addition of reducing sugar residues to proteins via covalent addition to amine functional groups located on amino acid sidechains. Following initial addition, several structural rearrangements occur which can result in intra- and intermolecular crosslinking of proteins [Brownlee in *Diabetes Mellitis Theory and Practice*, Rifkin, H and Porte, Jr, D, eds. (New York, Elsevier, 1990) pp. 279–291]. This is a complex series of non-enzymatic reactions which are not completely defined at this time. Yet, as discussed in U.S. patent application Ser. No. 08/026,617, there is reason to believe that this phenomenon is involved in diabetic vascular changes, diabetic nephropathy, cataracts, diabetic retinopathy and other secondary diabetic symptomology. Such reactions may also underlie much of the biochemistry of aging [Pongor et al. *Proc. Natl. Acad. Sci.* (USA) 81:2684–2688 (1984)].

The nature of the chemical bonds responsible for holding together the neurofibrillary tangles of Alzheimer's disease and other neurodegenerative diseases is still poorly understood. What limited information is publicly available on this question is compatable with the overall inventive concept of U.S. patent application Ser. No. 08/026,617; that cytotoxic consequences result from various forms of spurious covalent bond protein crosslinking, at least some forms of which may be clinically treated by the pharmacological procedures described therein.

Both AD senile plaques and neurofibrillary tangles consist largely of networks of intermediate size protein filaments helically wound in pairs having a periodicity of 80 nm [Selkoe et al. *Science* 215:1243–1245 (1982)]. Isolated paired helical filament (PHF) has proven to have remarkable properties of chemical stability. PHF chemical crosslinking bonds are not broken by sodium dodecyl sulfate, β-mercaptoethanol, 9.5 M urea, two percent Triton X-100, one percent NP-40, 6 M guanidine hydrochloride, 0.2 N HCl or 0.2 N NaOH. As heating of PHF in the presence of either reducing agents such as β-mercaptoethanol or detergents such as Triton X-100 or NP-40 did not solubilize PHF, bonds other than disulfide are implicated in amino acid crosslinking of this type of rigid intracellular polymer. This unusual chemical stability has seriously impeded PHF analysis by gel electrophoresis [Selkoe et al. *Science* 215:1243–1245 (1982)]. As a postulated mechanism for such unusual crosslinking Selkoe and coworkers noted that "different protein polymers in senile cataracts, terminally differentiated epidermal cells, and red blood cells are covalently crosslinked by gamma-glutamyl-epsilon-lysine sidechain bridges." Like PHF, these other protein complexes are insoluble in sodium dodecyl sulfate and not solubilized by reducing agents. Selkoe and coworkers speculated that such gamma-glutamyl-epsilon-lysine crosslinks may also form pathologically in nerve cells, as human brain contains a transglutaminase capable of acting on normal neurofilament to form an insoluble high molecular weight filamentous polymer.

The inventor has thoroughly and broadly disclosed the general concept of clinically treating the category of neurodegenerative diseases and pathophysiologically symptomology noted above by use of compositions consisting of carbonyl trapping (i.e., carbonyl sequestering) drugs, either alone or in combination with various co-agents, as a general approach to the treatment of these disease states. This disclosure of the general therapeutic concept was the subject of the inventor's publication, "Carbonyl-Trapping Therapeutic Strategies" [*Am. J. Therapeutics* 5:323–353 (1998)].

OBJECTS OF THE INVENTION

Accordingly, it is a general object of this invention to treat neurological diseases and etiologically related symptomology by use of primary agents that are carbonyl trapping substances in combination with non-absorbable polyamine carbonyl trapping substance co-agents; antioxidant co-agents; vitamin co-agents; co-agents that are metabolites at risk of depletion; sulfhydryl agents co-agents, and co-agents consisting of substances which may facilitate glutathione activity, and in combination with various additional effective medicament co-agents which have been shown to contribute to the alleviation of symptomology of the subject disease states as disclosed herein, so as to overcome the disadvantages of the prior art.

In particular, it is an object of the present invention that the drug compositions originally described in U.S. patent application Ser. No. 07/660,561 may be combined with medicaments effective to treat one or more of the underlying diseases addressed herein so as to provide increased clinical value in the treatment of disease symptomology for disorders featuring well defined neurofilament associated pathology, lipofuscin accumulation and/or aberrant lipid peroxidation, including diabetic polyneuropathy and related metabolic symptomology; Alzheimer's presenile/senile dementia; Down's syndrome; Parkinson's disease; amyotrophic lateral sclerosis; age-related atrophy of peripheral sensory and motor nerves, autonomic nerves, and neurons of the central nervous system, and pathophysiologically related changes in the cardiovascular system, kidney, and optic lens; alcoholic polyneuropathy; multiple sclerosis; olivopontocerebellar atrophy; Huntington's disease and disorders clinically related thereto.

It is another object of the present invention that insofar as the therapeutic procedures described herein may serve to delay the necessity of initiating the use of medicaments effective to treat the underlying disease or to decrease the dosages of said medicaments required to achieve beneficial effects, the period of prior art drug therapeutic value may be extended and detrimental clinical side effects resulting from use of said medicaments may be decreased, so that overall patient treatment may be improved.

It is another object of the present invention that insofar as the therapeutic procedures described herein may be of benefit for improvements in autonomic nervous system function, it is claimed that such procedures may better ameliorate symptomology of urinary incontinence.

It is yet another object of the present invention that insofar as the therapeutic procedures described herein may serve to covalently bind and sequester agents which may underlie, in part, the etiology of atherosclerosis, it is believed that such procedures may be of benefit in treatment of this pathophysiologically related disorder.

It is a further object of this invention that the absorbable primary amine substances described herein when used in combination with specified co-agents may be clinically applied to treat veterinary disorders comparable to those human disorders described above.

Use of a closed group of primary agents that are orally administered absorbable substances; a closed group of orally administered non-absorbable polyamine carbonyl trapping substances; a closed group of antioxidant co-agents; a closed group of vitamin co-agents; a closed group of co-agent metabolites at risk of depletion; and a closed group of sulfhydryl agents co-agents, including those originally disclosed in U.S. patent application Ser. No. 08/026,617, is included in the present invention, in combination with use of various additional effective medicament co-agents which have been shown to contribute to the alleviation of symptomology of the diseases addressed herein. In addition, the present invention includes use of a closed group of co-agents consisting of substances which may facilitate glutathione activity, including those originally disclosed in U.S. patent application Ser. No. 08/883,290, insofar as these co-agents further serve to improve the invention described in U.S. patent application Ser. No. 08/026,617.

DETAILED DESCRIPTION OF THE PREFERRED EMBODIMENT

It is understood that the therapeutically effective dosage ranges of primary agents and co-agents disclosed below apply to use by adult human subjects, and that such dosage ranges can be adapted on a kilogram body weight basis (assuming adult human weight from 45 kg to 136 kg) to use by non-adult humans or veterinary mammalian subjects. Furthermore, it is understood that the route of administration of any primary agent or co-agent of the present invention is limited to the oral route, unless otherwise stated.

The points of novelty and utility of this invention are the disclosure of a method for use of compositions consisting of primary agents which are absorbable carbonyl trapping drugs in combination with co-agents that may reasonably be expected to increase the therapeutic value of the primary agents for treatment of neurodegenerative diseases and pathophysiologically symptomology. The inventor discloses herein the novelty of combining the present primary agents and co-agents based on his heretofore unrecognized understanding of the unique value in terms of clinical utility to be anticipated, based on different and complimentary mechanisms of action of said primary agents and co-agents.

1. Physiological Basis of the Invention

These and other objects of this invention are achieved by providing a novel method for clinical treatment of neurological diseases and etiologically related clinical symptomology. While the causes of these diseases are diverse and largely undefined at present, these disorders nevertheless share many common characteristics at the cellular level.

For any one neurological disease certain nerve cells, usually with a characteristic anatomical distribution, will undergo a process of intracellular deterioration, eventually leading to cell death. In this process certain normal intracellular structures are progressively altered in terms of structure, as apparent by electron microscopy, and function, as indicated by enzyme activities. In addition, certain pathological structures, not normally present, will appear and usually develop in terms of number and size until they come to dominate the intracellular environment. These neuropathological changes end in cell death.

Biomedical information now publicly available indicates or suggests that spurious, pathological chemical crosslinking of normal intracellular structures is a fundamental aspect of the neurological diseases addressed herein. Such covalent bond crosslinking of protein and lipid subcellular elements appears to underlie the formation of at least four common neuropathological structures: (1) polymerized aggregates of structural protein filaments (e.g., excess neurofilament accumulation), (2) heterogeneous protein aggregates (e.g., neurofibrillary tangles), (3) amorphous protein and lipid aggregates (e.g., senile plaques), and (4) lipofuscin granules, which are amorphous aggregates rich in lipid chemical complexes. Spurious, excess protein chemical crosslinking is also apparent in the extracellular compartment in some of these diseases, for example, blood capillary basement membrane thickening in long term diabetes mellitus. In addition, analogous pathological chemical crosslinking of DNA can also occur under certain circumstances, thus further damaging cells prone to such attack. Based on the presence of one or more of the neuropathological events noted above, the drug treatment protocols falling within the scope of this invention may be of benefit to patients having one of the diseases addressed herein.

Moving to the chemical level, considerable biomedical literature indicates that certain sites on normal proteins and lipids are specific targets for spurious chemical crosslinking, most notably the $\epsilon$-amino groups of lysine residues in proteins and the amine groups of phosphatidylethanolamine molecules in cell lipid membrane bilayers. These primary amine groups are especially prone to attack by small molecular weight carbonyl-containing hydrocarbons. Such carbonyl-containing molecules may originate by many pathological mechanisms still only partly defined, but, in general, they originate from peroxidation of fatty acids or as by-products of sugar metabolism. A monocarbonyl specie can bind to a protein or amino-lipid, alter its three dimensional structure and possibly affect its chemical activity. A dicarbonyl hydrocarbon can react with two amine groups, thus making a covalent chemical crosslink. The specific primary pathological changes which underlie this type of deterioration remain largely undefined, but their structural products have been characterized in many respects.

Kikugawa and Beppu [*Chem. Phys. Lipids* 44:277–296 (1987)] noted that lipid radicals, hydroperoxides and their secondary products react with neighboring protein molecules, damaging protein structure and function. Such damage includes formation of fluorescent chromophores, lipid-protein adducts, and protein-protein crosslinks. Using sodium dodecyl sulfate-polyacrylamide gel electrophoresis, these investigators demonstrated that malonaldehyde (also known as malondialdehyde), a bifunctional molecule having two aldehyde groups, can covalently crosslink proteins. This reaction primarily involves Schiff base formation with protein ε-amino groups on the sidechains of lysine residues. Kikugawa and Beppu (1987) also reported that monofunctional aldehydes such as acetaldehyde, 1-hexanal, 1-heptanal and 2,4-decadienal can also crosslink proteins, generating fluorescent products. This biochemical curiosity still not well understood. Some form of self-condensation may be involved.

The generation of water soluble, carbonyl-containing products of lipid peroxidation can be readily demonstrated under simple in vitro conditions. Schauenstein [*J. Lipid Res.* 8:417–428 (1967)] incubated suspended polyunsaturated fatty acid esters with water at 40° C. in the presense of air and demonstrated the generation of numerous such products. These included oct-2-trans-en-1-al, 4-hydroperoxynon-2-en-1-al,1-hydroxyheptan-2-one,4-hydroxy-2-trans-octen-1-al, as well as numerous other water soluble products not characterized in Schauenstein's investigation. Other investigators have also documented the generation of numerous carbonyl-containing products of lipid peroxidation, however the exact identities of many of these agents remains undefined [Esterbauer et al. *Biochem. J.* 208:129–140 (1982)].

The conceptual similarities between lipid peroxidation-induced protein crosslinking and protein crosslinking associated with non-enzymatic glycosylation has been noted in the research literature [Kikugawa and Beppu *Chem. Phys. Lipids* 44:277–296 (1987)]. Some evidence has been presented which suggests that a slow, age-dependent deterioration of biological systems which counteract lipid peroxidation may be a fundamental part of the aging process [Harman *J. Gerontol.* 26:451–457 (1971)]. This concept is sometimes referred to as the free radical theory of aging.

A variety of furans, aldehydes and ketones have been identified in normal human urine [Zlatkis and Liebich *Clin. Chem.* 17:592–594 (1971); Matsumoto et al. *J. Chromatoqr.* 85:31–34 (1973)]. These include 2,5-dimethyl furan, 2-methyl furan, other alkyl furans, and a variety of five- to eight-carbon alkyl aldehydes and ketones. Yancey et al. [*J. Chromatogr.* 382:47–56 (1986)] induced lipid peroxidation in rats by use of a defined diet deficient in both vitamin E and selenium, and then studied volatile urine metabolites. The results showed that urine of vitamin E deficient animals contained 16 carbonyl compounds which were present at elevated levels of statistical significance. The greatest increases observed were for hydroxy-acetylaldehyde (676%), benzaldehyde (538%) and furfural (487%). In discussing their findings, Yancey et al. concluded, in part:

> Both capillary GC and LC results appear to implicate aldehydes (both normal and unsaturated) and related compounds, furan derivatives, as characteristic products of lipid peroxidation. Elevated aldehyde levels were also noticed in our earlier investigations of urinary metabolites of both long-term diabetic rats and genetically diabetic mice. Since an increased lipid peroxidation process has been associated with the diabetic condition, it is not surprising that known peroxidation metabolites should be more abundant in diabetic than normal urine samples . . . Increased lipid peroxidation clearly results in a greater production of metabolites that are either proven or suspected neurotoxins.

Non-enzymatic in vitro autoxidation of furfural has been described, which yields a mixture of products which includes 2-furoic acid [Dunlop and Peters *The Furans* (New York, Reinhold Publishing, 1953) pg. 385]. Likewise, Williams [*Detoxication Mechanisms: The Metabolism and Detoxication of Drugs, Toxic Substances and Other Organic Compounds* (New York, John Wiley & Sons, 1959) pp. 550–551] has described the mammalian in vivo oxidation of 2,5-dimethyl furan to 5-methyl-2-furoic acid and of 5-hydroxymethyl-furfural to 5-hydroxymethyl-2-furoic acid. In principle, the process of enzymatically converting hydrocarbon functional groups such as a methyl group of 2,5-dimethyl furan to a carboxylic acid group involves three consecutive oxidation reactions.

As summarized above, and discussed at greater length in U.S. patent application Ser. No. 08/026,617, 2,5-dimethyl furan is a recognized secondary product of lipid peroxidation and there is reason to believe that it may be oxidized in vivo to products such as 5-hydroxymethyl-2-furancarboxylic acid and 2,5-furandicarboxylic acid. This, in turn, suggests that 5-hydroxymethyl furfural and 2,5-furandialdehyde may be metabolic intermediates in this process.

It is the unique belief and understanding of this inventor that the long term generation of furan aldehyde agents as by-products of lipid peroxidation can serve as a metabolic basis or underlying contributing factor in the etiology of diabetic symptomology, the etiology of other neurological diseases featuring evidence of Schiff base type chemical crosslinking phenomena, and in the etiology of age-related symptomology. It seems reasonable to this inventor that the chromosome 17 HMSN patients discussed above were experiencing toxic long term consequences of furanaldehyde exposure as a consequence of defective ability to oxidize furanaldehydes which are normal products of lipid metabolism. Failure to dispose of these reactive metabolites efficiently may predispose the patients to a decline in clinical status initiated by pathological protein crosslinking. For diabetic patients, on the other hand, excess levels of furanaldehyde metabolites seem to appear as a consequence of chronic hyperglycemia. It appears that in the diabetic state in vivo capacity to oxidize or otherwise detoxify furanaldehydes is simply exceeded by endogenous generation of these toxic metabolites. Thus there does appear to be a degree of similarity between these two disease states, reflected in similar peripheral neuropathies, yet their metabolic origins appear to be different.

The present invention discloses protocols of drug therapy for treatment of the medical disorders addressed herein. As originally described in U.S. patent application Ser. No. 07/660,561, these pharmacological reactions are based on the ability of primary amine agents to react stoichiometrically with aldehyde functional groups of potentially toxic agents, yielding covalently bound Schiff base products (see Section 2. Mechanism of Action of Primary Agents Useful in the Present Invention, below), and one may add to the beneficial effects of said treatment by compounding the primary agent with various co-agents.

U.S. patent application Ser. No. 08/026,617 sets forth that absorbable pharmaceutical agents such as p-aminobenzoic acid when administered to humans in oral dosages of from one gram/day to 40 grams/day may be used as therapeutic agents for treatment of certain neurological diseases and for treatment of other pathophysiologically related clinical phenomena. U.S. patent application Ser. No. 08/026,617 also comprises use of orally administered, non-absorbable polyamine polymeric co-agents such as chitosan for use in treatment of the disease entities noted above. Such non-absorbable pharmacological co-agents may act to covalently bind and sequester potentially toxic carbonyl compounds present in the diet. In addition, U.S. patent application Ser. No. 08/026,617 comprises the use of such chemical agents and co-agents in combination with antioxidants such as α-tocopherol, suspending reagents such as carboxymethyl cellulose for the compounding of oral tablets, other vitamins, and chemical conjugating co-agents which may facilitate kidney drug elimination, such as glycine. The present disclosure describes the inventive concept of using the therapeutic technology of U.S. patent application Ser. No. 08/026,617 in combination with pharmaceutical agents recognized as having, or possibly having some medicinal value for treatment of the disease entities noted above.

2. Mechanism of Action of Primary Agents Useful in the Present Invention

The pharmacological reactions of the present invention are based on the ability of primary amine compounds to react with aldehyde functional groups of potentially toxic agents, yielding covalently bound Schiff base products. Several examples of chemically analogous reactions, presented within other contexts, have been publicly presented. Representative examples are discussed below. These model chemical systems are directly analogous to the proposed mechanism of drug action of the primary agents of the present invention.

Comments by Feeney and coworkers [Adv. Protein Chem. 29:135–203 (1975), pg. 141] provide an appropriate introduction to this subject:

A wide variety of substances with —NH$_2$ groups condense with carbonyl compounds . . . This condensation of primary amines with aldehydes and ketones to give imines was first discovered by Schiff (1900). The overall equilibrium greatly favors hydrolysis in aqueous solution for aliphatic aldehydes. With aromatic aldehydes, the equilibrium is shifted in favor of Schiff base formation. It is important to note that increasing the nucleophilic strength of the amine will increase the rate of the carbonylamine reaction but will have almost no effect on the position of the equilibrium.

These comments suggest that the amine-containing carbonyl-trapping drugs that are the primary agents described herein should have particular promise for binding furanaldehydes, which are aromatic. These comments also suggest that doses of primary agent absorbable amine drugs may require in vivo concentrations in the range of 1:100 to 1:1,000 (carbonyl:amine) in order to achieve clinical effectiveness. This, in turn, suggests that therapeutic dosages for adult human subjects lie in the range of grams per day and that only drugs of particularly low toxicity will have human applications.

Feeney and coworkers (1975, pg. 144) also noted the phenomenon of Schiff base transimination, which occurs to a significant extent at neutral pH:

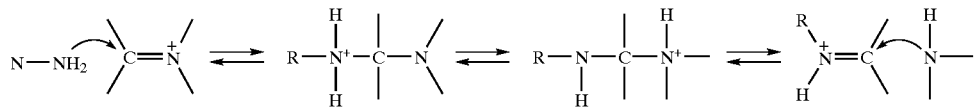

The existence of such non-enzymatic reversible transimination reactions is important within the context of this invention, as it suggests that in vivo both bound carbonyl agents, in addition to free carbonyl agents, may be sequestered by amine-containing drugs.

(a) The direct in vitro addition of p-aminobenzoic acid or ethyl p-aminobenzoate to malondialdehyde or its tautomer, β-hydroxyacrolein, has been described [Sawicki et al. Anal. Chem. 35:199–205 (1963)].

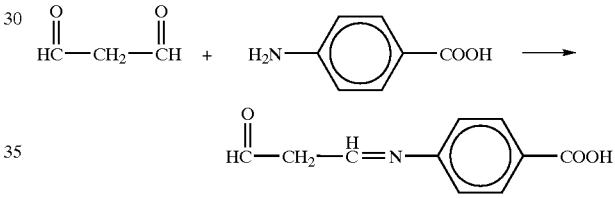

The metabolic fate of PABA in humans has been actively investigated and well reported in the biomedical literature [Young et al. Clin. Chem. 17:765–773 (1971); Howie and Bourke Clin. Sci. 56:9–14 (1979)]. It is so actively metabolized via several mechanisms and quantitatively removed in urine [Weizman et al. Gastroenterology 89:596–604 (1985); Bingham and Cummings Clin. Sci. 64:629–635 (1983)] that PABA excretion has become a widely recognized standard for measuring urinary clearance. Small amounts of PABA are normally present in the human diet. It is recognized as being a vitamin for many organisms and is classified as a member of the vitamin B complex [Smith Greenfield's Neurology, Blackwood, W and Corsellis, JAN, eds. (Chicago, Year Book Medical Publishers, 1976) pp. 194; Winitz et al. Am. J. Clin. Nutr. 23:525–545 (1970), pgs. 527–528; Scott and Robbins Proc. Soc. Exp. Biol. Med. 49:184–186 (1942)]. As a vitamin for human use PABA is commercially marketed in the dosage range of 5 to 550 mg/day.

(b) The direct in vitro addition of n-hexylamine to β-hydroxyacrolein to produce an N,N'-disubstituted 1-amino-3-iminopropene derivative has been reported [Chio and Tappel Biochemistry 8:2821–2827 (1969)]. The reaction may be represented as follows:

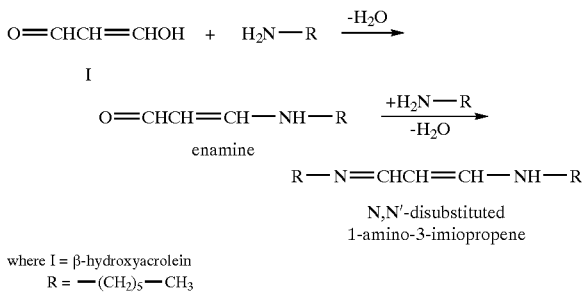

where I = β-hydroxyacrolein
R = —(CH$_2$)$_5$—CH$_3$ (c) The direct chemical addition of amines to 5-methyl-2-furfural has been described (Holdren, R F and Hixon, R M, 1946). A wide variety of aliphatic and aromatic primary amines can add to furfural in this manner, yielding Shiff base products [Dunlop and Peters *The Furans* (New York, Reinhold Publishing, 1953), pg. 353].

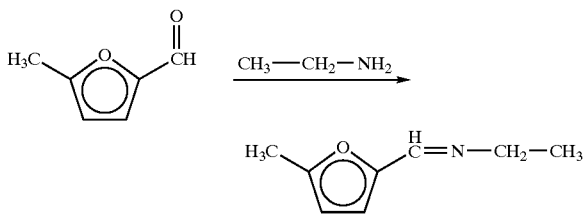

(d) As described by Dunlop and Peters [1953, pg. 373] earlier work demonstrated the ability of furfural to react with aminosulfonic salts to produce furfurylideneaminosulfonates:

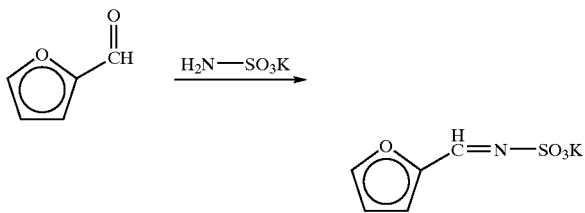

(e) The reaction of phenylaminoguanidine with furfural [Dunlop and Peters, 1953, pg. 371] may serve as an example of covalent furanaldehyde trapping with a hydrazine.

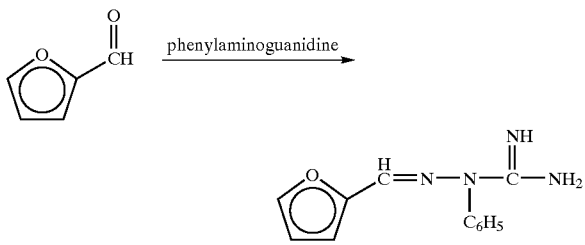

(f) Self-polymerization of o-aminobenzaldehyde has been described. In the 1994 edition of the Sigma Chemical Company catalog of biochemical reagents the following statement appears on page 90 of its listing: "o-AMINOBENZALDEHYDE Unstable! [store at] −20° C. Polymerizes rapidly when exposed to room temperature. May yield slightly hazy solution in ethanol due to presence of a small amount of polymer. Shipped in dry ice." This information directly indicates that a primary amino group covalently linked to a benzene ring possesses sufficient reactivity for significant reaction with aldehyde functional groups at room temperature. It is apparent that no form of activation of the amino group is required and that a Schiff base product forms readily.

The small molecular weight, absorbable, primary amine-containing drugs and amine-related drugs to be administered via the oral route as primary agents described herein have analogous behavior in vivo, as well as an additional characteristic which will facilitate disposal as urine metabolites. All of these drugs contain a carboxylic acid group to facilitate uptake and processing by the kidneys.

3. Examples of the Primary Agents of the Present Invention: A Closed Group of Orally Administered Absorbable Carbonyl Trapping Substances It is the central premise of U.S. patent application Ser. No. 08/026,617 that an opportunity exists, heretofore unrecognized, for pharmacological intervention in some neurological diseases by use of water soluble, small molecular weight primary amine agents and chemical derivatives thereof. Such pharmacological agents, administered orally, can compete with cellular protein and lipid amine groups for reaction with disease-induced carbonyl-containing hydrocarbons. Such derivatized pharmacological agents can then be excreted by the kidneys. This process, while not necessarily addressing the primary etiology of a neuropathy, may be of practical clinical benefit to significantly delay the onset of a disease, stop disease progression for an extended period, or lead to observable improvement in patient status.

Ideally, such an absorbable pharmacological agent should have several characteristics. It should be water soluble and of small molecular weight so that it can passively and readily diffuse throughout the body, including within cells. It should have at least one chemically active trapping group, such as a primary amine group (R—NH$_2$), for reaction with carbonyl groups (R—CHO or R$_1$—CO—R$_2$) to yield covalent bonded products. It should otherwise not interact with normal cell metabolism or do so in ways which are not cytotoxic. It should be tolerated by the body in relatively high dosages (range of grams per day) and for extended periods. In addition, such an absorbable pharmacological agent and its metabolic derivatives should be readily absorbed by kidney tissue and excreted in urine without nephrotoxic consequences.

In a preferred embodiment, the therapeutically effective amount of the primary agent of the present invention for the adult human subject is a dosage in the range of from about 15 mg/kg/day to about 450 mg/kg/day, more preferably from about 20 mg/kg/day to about 450 mg/kg/day, and most preferably from about 40 mg/kg/day to about 450 mg/kg/day.

4-Aminobenzoic acid (also known as p-aminobenzoic acid or PABA) is an example of the absorbable primary agent of this invention. PABA has a small molecular weight (137, free acid) and is water soluble. It has a primary amine group which should readily react with carbonyl-containing metabolites under physiological conditions. PABA has already been commercially marketed for other health applications and it has been used effectively and safely by millions of people. It has been used as a popular sun screen topical cream additive and its potassium salt has also been used as an antifibrotic prescription drug for treatment of Peyronie's disease, diffuse systemic sclerosis, morphea, linear scleroderma and dermatomyositis. On a prescription basis the potassium salt of PABA is recognized for use in a dosage of 12–20 grams/day for up to two years [Zarafonetis *Texas State J. Med.* 49:666–672 (1953)]. As an ingredient in analgesic tablets, PABA has been marketed for domestic human use (300 mg/tablet) in PABIRIN® buffered tablets (with aspirin), in PABALATE® tablets (with sodium salicylate) and in PABALATE-SF® tablets (with potassium salicylate), as described in *Physicians' Desk Reference* (Huff, 1980, pgs. 849, with aspirin and 1430, with salicylates).

The metabolic fate of PABA in humans has been actively investigated and well reported in the biomedical literature. It is so actively metabolized via several mechanisms and quantitatively removed in urine that PABA excretion has become a widely recognized standard for measuring urinary clearance. Small amounts of PABA are normally present in the human diet. It is recognized as being a vitamin for many organisms and is classified as a member of the vitamin B complex. As a vitamin for human use PABA is commercially marketed in the dosage range of 5 to 550 mg/day.

For any of the chemical derivatives of PABA listed herein as useful in the present invention, it is believed that the pharmaceutically acceptable salt, free acid, pharmaceutically acceptable ester and analogous non-aromatic ring derivatives (i.e., cyclohexadiene, cyclohexene or cyclohexane carboxylic acid derivatives) thereof will also be useful. The PABA derivatives are

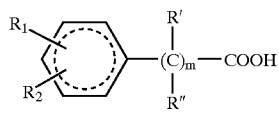

wherein the 6-membered ring is phenyl, cyclohexadiene, cyclohexene or cyclohexane; and wherein $R_1$ is selected from the group consisting of —$NH_2$; ε-aminoalkyl having 1–10 carbons linear or branched and hydroxylated derivatives of this structure; —NHC(=NH)$NH_2$; —$(CH_2)_n$NHC(=NH)$NH_2$ wherein n is 1–10 hydrocarbons linear or branched and hydroxylated derivatives of this structure; —C(=NH)$NH_2$; —$(CH_2)_n$—CH=NH(=NH)$NH_2$ wherein n is 1–10 hydrocarbons linear or branched and hydroxylated derivatives of this structure; —NHC(=NH)NH$NH_2$; —$(CH_2)_n$NHC(=NH)NH$NH_2$ wherein n is 1–10 hydrocarbons linear or branched and hydroxylated derivatives of this structure; —$(CH_2)_n$—CH=NC(=NH)NH$NH_2$ wherein n is 1–10 hydrocarbons linear or branched and hydroxylated derivatives of this structure; —NHNHC(=NH)$NH_2$; —$(CH_2)_n$—NHNHC(=NH)$NH_2$ wherein n is 1–10 hydrocarbons linear or branched and hydroxylated derivatives of this structure; and —$(CH_2)_n$—CH=N—NHC(=NH)$NH_2$ wherein n is 1–10 hydrocarbons linear or branched and hydroxylated derivatives of this structure thereof;

$R_2$ is selected from the group consisting of H; —$NH_2$; —OH; —O—$CH_3$; —OR' wherein R' is alkyl of 2–10 hydrocarbons linear or branched and hydroxylated derivatives of this structure; ε-aminoalkyl wherein the alkyl group is 1–10 hydrocarbons linear or branched and hydroxylated derivatives of this structure; —$SO_3H$; —$CH_3$; and —$(CH_2)_n$$CH_3$ wherein n is 1–10 hydrocarbons linear or branched and hydroxylated derivatives of this structure; and R' and R" are H, —OH or —$CH_3$; and m is 0 or 1.

4. Mechanism of Action of Orally Administered Non-Absorbable Co-Agents Useful in the Present Invention The presence of aldehydes and ketones in the human diet also is a factor which may put the patient suffering from a neurodegenerative disease or pathophysiologically related symptomology further at risk. 5-Methyl furfural has been identified in the oil of roasted coffee and in oil of cloves [Dunlop and Peters, 1953, pg. 403]. 5-Hydroxymethyl furfural has been found in sherry, port and brandy alcoholic beverages; honey and other sugar syrup products [Lever et al. *Anal. Biochem.* 144:6–14 (1985)]. Levels of furfural (i.e., 2-furanaldehyde or 2-furancarboxaldehyde) and 5-hydroxymethyl-2-furanaldehyde (i.e., 5-hydroxymethyl furfural) as high as 4.5 mg/L and 93.2 mg/L, respectively, have been found in wine products [Shimizu and Watanabe *Agric. Biol. Chem.* 43:1365–1366 (1979)]. Furfural has also been detected in beer and distilled liquors [Dunlop and Peters, 1953, pg. 308], as well as in natural oil products such as oil of lime [Dunlop and Peters, 1953, pg. 280]. Summarizing earlier work, Rice [*Clin. Chem.* 18:1550–1551 (1972)] noted:

Small quantities of furfural occur in many foodstuffs, including—among many others—bread, coffee, processed fruits and fruit juices, and alcoholic beverages. In fact, whenever plant or animal tissue containing pentoses or hexoses is subjected to heat, the possibility arises that furfural, 5-hydroxymethyl furfural, and probably other furans as well will be produced.

Pettersen and Jellum [Clin. Chim. Acta 41:199–207 (1972)] referred to earlier work which demonstrated the generation of 2-furanaldehyde, 5-hydroxymethyl-2-furanaldehyde and 2,5-furandicarboxaldehyde during bread baking. In his food chemistry study, Baltes [*J. Anal. Appl. Pyrol.* 8:533–545 (1985)] noted the presence of furfural in curing smoke tar; and the presence of furfural, 5-methyl-2-furfural, dihydrofuranone, 5-hydroxymethyl-2-furfural and 2,5-furandialdehyde in caramels. Baltes also examined the products obtained by Maillard reaction of glucose and phenylalanine and identified furfural and 2,5-di-(hydroxymethyl)-furan among the main components. Thus various furan aldehyde compounds have been identified in the human diet.

In addition, a wide variety of naturally occurring non-aromatic and aromatic aldehydes and ketones have been found in fruits and vegatables (Schauenstein and Esterbauer [*Aldehydes in Biological Systems. Their Natural Occurrence and Biological Activities* (London, Pion Limited, 1977), pgs. 181–194]. These include alkanals, alk-2,4-dienals, alk-2-enals, alk-1-en-3-ones, α-dicarbonyl compounds, β-dicarbonyl compounds alkan-2-ones. Schauenstein and Estabauer have noted, in part, that:

Aliphatic carbonyl compounds represent the most important group of flavouring compounds in our foodstuffs. One finds them in all flavour extracts. They are either entirely, or in large measure, responsible for nearly all known flavours and determine, even when present in small amounts, the taste and odour of our foodstuffs, and beverages such as tea and coffee . . . (pg. 189)

As the presence of carbonyl agents in the diet is not restricted to fruits and vegatables, Schauenstein and Estabauer have further noted that:

Unsaturated aldehydes also arise through thermal degradation of carbohydrates, amino acids, and fats.

Such thermal degradative processes are probably responsible for the presence of these aldehydes in boiled, fried, and baked foods. Unsaturated aldehydes have been detected in a large number of foodstuffs, such as potatoes, potato chips, poultry, meat, fish, salad oils, bread, and bakery products . . . (pgs. 193–194)

As such, it is apparent that the diet is a significant source of carbonyl agents, and their presence may be a contributing factor in the etiology of chronic inflammatory diseases. Toxic properties of furanaldehyde derivatives have been demonstrated in both in vivo and in vitro studies [Konecki et al. *Folia Histochem. Cytochem.* 12:59–66 (1974); Ulbricht et al. *Exp. Appl. Toxicol.* 4:843–853 (1984)]. Non-digestible polyamine-containing co-agents such as those defined below can be of health benefit by virtue of their ability to covalently trap dietary aldehydes and ketones. The co-agents described in this section can accomplish this function because they bear primary amine groups. As large molecular weight molecules which are non-digestible they have the capacity to pass through the digestive tract, acting in effect as another form of dietary fiber. These non-absorbable carbonyl trapping substances may include naturally occurring polyamine polysaccharides, chemical derivatives of naturally occurring polysaccharides, and synthetic polyamine polymers. The fate of malondialdehyde (MDA) given orally to rats may serve as an example of the metabolism of dietary aldehydes, and how an understanding of this process can be used to define non-absorbable carbonyl-trapping co-agents. Studies by Draper and coworkers [*Lipids* 21:305–307 (1986)] demonstrated that the primary form of "bound" MDA in rat or human urine is N-α-acetyl-ε-(2-propenal)lysine. This is the biologically acetylated derivative of the MDA-lysine adduct N-ε-(2-propenal)lysine, as shown below.

Draper and coworkers [1986] were able to generate N-ε-(2-propenal)lysine in vitro by exposing beef muscle protein to MDA, followed by treatment with pepsin and hog intestinal juice. This indicates that the ε-amino groups of dietary protein lysine

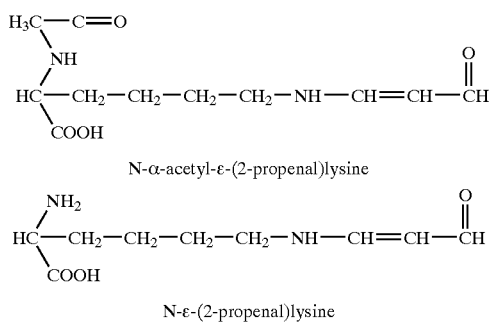

residues can covalently bind dietary aldehyde under conditions found in the intestinal tract. As such, chemically analogous primary amine groups on the non-absorbable co-agents of the present invention also are capable of covalently binding dietary aldehydes under conditions to be found in the intestinal tract. In this case, however, the bound carbonyl species are excreted in the feces, thus preventing subsequent in vivo exposure to dietary carbonyl agents.

In their study Draper and coworkers noted that N-α-acetyl-ε-(2-propenal)lysine was found in urine of fasted rats or animals fed on MDA-free diets, indicating that the MDA-lysine adduct also forms in vivo. These investigators referred to earlier work which demonstrated that the MDA concentration normally found in food is in the range of <0.1 to 10 ppm (0.1 to 10 μM), which gives some idea of dietary aldehyde concentrations.

5. Examples of Non-Absorbable Co-Agents Useful in the Present Invention: A Closed Group of Orally Administered Non-Absorbable Polyamine Carbonyl Trapping Substances As discussed in U.S. patent application Ser. No. 08/026,617, the diet is a significant source of carbonyl agents. These agents may be contributing factors in the aging process, may predispose humans for other neurodegenerative disorders, may be contributing factors in atherosclerosis, may be contributing factors in inflammatory diseases and may also be contributing factors in the initiation of carcinogenesis. Such carbonyl agents, while contributing positively in some instances to the flavor of foods or beverages (for example, cheeses or wines), have no recognized nutritional value. It was proposed in U.S. patent application Ser. No. 08/026,617 that certain dietary supplements can be of public health benefit by their ability to covalently trap dietary aldehydes and ketones. The co-agents described in this subsection can accomplish this function because they bear primary amine groups or derivatives thereof. As large molecular weight molecules which are non-digestible they have the capacity to pass through the digestive tract, acting in effect as another form of dietary fiber.

In a preferred embodiment, the therapeutically effective amount of an orally administered non-absorbable polyamine carbonyl trapping substance co-agent of the present invention for the adult human subject is a dosage in the range of from about 15 mg/kg/day to about 450 mg/kg/day, more preferably from about 20 mg/kg/day to about 450 mg/kg/day, and most preferably from about 40 mg/kg/day to about 450 mg/kg/day.

As defined in the original filing of U.S. patent application Ser. No. 07/660,561, examples of these non-absorbable polyamine trapping substances may be divided into three classes; naturally occurring polyamine polysaccharides, chemical derivatives of naturally occurring polysaccharides, and synthetic polyamine polymers.

(a). Naturally Occurring Amine-Containing Polysaccharides

Any naturally occurring polysaccharide featuring β-1,2, β-1,3, β-1,4 and/or β-1,6 linkages which contains amino-sugars may be regarded as a non-digestible, potentially active carbonyl trapping agent. The chitin class of biopolymers may be cited as an example of such an agent, having the general structure of

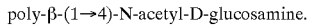

poly-β-(1→4)-N-acetyl-D-glucosamine.

A form of microcrystalline chitin has been described in which some of the acetyl groups have been removed, revealing free amine groups [Austin et al. *Science* 212:749–753 (1981)]. Chitins obtained from different sources feature different degrees of amine deacetylation [Austin et al. *Science* 212:749–753 (1981)].

(b). Chemical Derivatives of Naturally Occurring Polysaccharides

Various pretreatment procedures may be applied to naturally occurring polysaccharides prior to generation of chemical derivatives. Generation of microcrystalline polysaccharides is one example of such a pretreatment procedure. As applied to cellulose or chitin [Yalpani *Polysaccharides: Syntheses, Modifications and Structure-Property Relations* (New York, Elsevier, 1988) pg. 389], this yields a colloidal processed form of polysaccharide featuring high porosity and enhanced susceptibility to chemical reactions. Generation of "microfibrillated" cellulose or chitin is another example of a pretreatment procedure which produces enhanced surface area, increased water retention capacity and enhanced chemical accessibility [Yalpani (1988) pg. 390]. Use of strong (>18%) sodium hydroxide is still another recognized pretreatment, or activation, procedure found to be helpful as a starting point for preparing chemical derivatives of polysaccharides [Yalpani (1988) pg. 214].

(b)(1). Deacetylation of Naturally Occurring Polysaccharides.

A variety of polysaccharides have been identified which are rich in N-acetylated residues. Upon chemical deacetylation these carbohydrates yield high molecular weight derivatives bearing primary amine groups directly linked to sugar carbons, that is, no sidearm spacer units present.

(i) Chitosan. This is the deacylated form of chitin. As described in the Merck Index, 11th ed. [Budavari et al. (Rahway, N.J., Merck & Co., 1989) pg. 316] chitin is a cellulose-like biopolymer the composition of which consists mostly of N-acetyl-D-glucosamine residues covalvently linked by β-1,4 bonds. Chemical deacylation removes acetate, generating primary amine groups still covalently bound to the polysaccharide. Chitosan has recognized uses in water treatment, in photographic emulsions, and in improving the dyability of synthetic fabrics and fibers. The free amine groups in this substance also give it chelating properties [Austin et al. *Science* 212:749–753 (1981)].

(ii) Chondroitin sulfate. This is a mucopolysaccharide found commonly in mammalian tissue. It consists of repeating disaccharide units, each of which has a D-glucuronic acid residue β-1,4 linked to an N-acetylchondrosine residue [Budavari et al. *Merck Index,* 11th ed. (Rahway, N.J., Merck & Co., 1989) pg. 344)].

(iii) Hyaluronic acid. This mucopolysaccharide is also found commonly in mammalian tissues. It consists of glucuronic acid and glucosamine residues bound by β-1,3 and β-1,4 linkages [Budavari et al. *Merck Index,* 11th ed. (Rahway, N.J., Merck & Co., 1989) pp. 751–752)].

(iv) Keratan sulfate. This mammalian glycosaminoglycan consists of a repeating disaccharide unit of a C-6 sulfated C-2 N-acetylated sugar residue and a galactose residue linked by β-1,4 bonds [Yalpani (1988) pp. 27–28].

(b)(2). Chemical Amination of Polysaccharides (i) 2-Amino-2-deoxy-cellulose. Cellulose can be aminated by a process of selective oxidation, oximation and subsequent reduction with lithium aluminum hydride [Yalpani (1988) pp. 281–282].

(ii) Alternative amination procedures. Aminodeoxy polysaccharides can also be prepared via azide or hydrazide intermediates or by reductive amination using sodium cyanoborohydride [Yalpani (1988) pg. 281]. Besides being applied to cellulose, other non-digestible polysaccharides such as curdlan [Yalpani (1988) pg. 22] may be aminated by such chemical procedures.

(iii) 3-Aminopropylcellulose. Reaction of cyanoethylcellulose with borane-tetrahydrofuran or borane-dimethyl sulfide complexes in tetrahydrofuran generates 3-aminopropylcellulose [Yalpani (1988) pp. 250 and 255]. In this derivative each primary amine group is at the end of a three carbon sidearm.

(iv) Aminoethylcellulose. This chemical has been previously marketed as an anion exchange column chromatography resin (Sigma Chemical Co. catalog, Feb. 1981) and used as such in protein purification studies [Fasold in *Chromatography: A Laboratory Handbook of Chromatographic and ElectroPhoretic Methods,* 3rd ed., Heftmann, E, ed. (New York, Van Nostrand Reinhold, 1975) pp 481–482].

(v) Other aminoalkyl-, amino(hydroxyalkyl)-, aminoalkyl-ether-, and amino(hydroxyalkyl)-ether-derivatives of cellulose, chitin and other naturally occurring non-digestible carbohydrates. Noting that the chemical methodology for producing such derivatives is documented in public domain literature, the biomedical application of such derivatives for therapeutic purposes described herein is also claimed. This would include:

aminoalkyl derivatives of the formula $H_2N-(CH_2)_2-$[carbohydrate] where n=1–30, including alkyl isomers;

amino(hydroxyalkyl)-derivatives derivatives of the formula $H_2N-(CH_2)_n-CHOH-(CH_2)_n$-[carbohydrate], where m=0–15 n=0–15;

aminoalkyl-ether-derivatives of the formula $H_2N-(CH_2)_n-O$-[carbohydrate], where n=1–30 amino(hydroxyaklyl)-ether-der-ivatives of the formula $H_2N-(CH_2)_n-CHOH-(CH_2)_n-O$-[carbohydrate], where m=0–15 n=0–15

(vi) Aminobenzyl-derivatives of cellulose, chitin or other naturally occurring non-digestible carbohydrates. As the aromatic amine group is a weaker base than its aliphatic counterpart, this class of non-absorbable amines should be less chemically active than amino- and aminoalkyl-derivatives described above. These derivatives are of the following general structures:

$H_2N-C_6H_4-(CH_2)_n$-[carbohydrate], $H_2N-CH_2-C_6H_4-(C_2)_n$-[carbohydrate], $H_2N-C_6H_4-(CH_2)_n-O$-[carbohydrate] where n=0–30, and $H_2N-C_6H_4-(CH_2)_m-CHOH-(CH_2)_n-O$-[carbohydrate] where m=0–15 n=0–15

This includes p-, o- and m-benzene ring amino- and aminomethylisomers, and alkyl group isomers.

(vii) guanidine and aminoguanidine derivatives of cellulose, chitin or other naturally occurring non-absorbable carbohydrates selected from the group consisting of:

$H_2N-C(=NH)$-[carbohydrate];

$H_2N-C(=NH)-(CH_2)_n$-[carbohydrate], where n=1–10, including hydrocarbon isomers and hydroxylated derivatives thereof;

$H_2N-C(=NH)-O-(CH_2)_n$-[carbohydrate], where n=1–10, including hydrocarbon isomers, ether linkage isomers and hydroxylated derivatives thereof;

$H_2N-C(=NH)-NH$-[carbohydrate];

$H_2N-C(=NH)-NH-(CH_2)_n$-[carbohydrate], where n=1–10, including hydrocarbon isomers and hydroxylated derivatives thereof;

$H_2N-C(=NH)-NH-(CH_2)_n-O$-[carbohydrate], where n=1–10, including hydrocarbon isomers, ether linkage isomers and hydroxylated derivatives thereof;

$H_2N-C(=NH)-N=CH-(CH_2)_n$-[carbohydrate], where n=1–10, including hydrocarbon isomers and hydroxylated derivatives thereof;

$H_2N-C(=NH)-N=CH-(CH_2)_n-O$-[carbohydrate], where n=1–10, including hydrocarbon isomers and hydroxylated derivatives thereof;

$H_2N-NHC(=NH)-NH$-[carbohydrate];

$H_2N-NHC(=NH)-NH-(CH_2)_n$-[carbohydrate], where n=1–10, including hydrocarbon isomers and hydroxylated derivatives thereof;

$H_2N-NHC(=NH)-NH-(CH_2)_n-O$-[carbohydrate], where n=1–10, including hydrocarbon isomers, ether linkage isomers and hydroxylated derivatives thereof;

$H_2N-NHC(=NH)-N=CH-(CH_2)_n$-[carbohydrate], where n=1–10, including hydrocarbon isomers and hydroxylated derivatives thereof;

$H_2N-NHC(=NH)-N=CH-(CH_2)_n-O-$[carbohydrate], where n=1–10, including hydrocarbon isomers, ether linkage isomers and hydroxylated derivatives thereof;

$H_2N-C(=NH)-NH-NH$-[carbohydrate];

$H_2N-C(=NH)-NH-NH-(CH_2)_2$-[carbohydrate], where n=1–10, including hydrocarbon isomers and hydroxylated derivatives thereof;

$H_2N-C(=NH)-NH-NH-(CH_2)_n-O$-[carbohydrate], where n=1–10, including hydrocarbon isomers, ether linkage isomers and hydroxylated derivatives thereof;

$H_2N-C(=NH)-NH-N=CH-(CH_2)_n$-[carbohydrate], where n=1–10, including hydrocarbon isomers and hydroxylated derivatives thereof;

$H_2N-C(=NH)-NH-N=CH-(CH_2)_n-O$-[carbohydrate], where n=1–10, including hydrocarbon isomers, ether linkage isomers and hydroxylated derivatives thereof;

(b)(3). Aminated Sucrose Polyesters

Mixtures of fatty acid hexa-, hepta- and octaesters of sucrose, known as sucrose polyester, are not hydrolyzed by pancreatic lipase enzymes and are not absorbed in the intestine [Jandacek Int. *J. Obes.* 8(suppl. 1):13–21 (1984)]. It is proposed and claimed herein that primary amine, aminoguanidine and guanidine derivatives of sucrose polyesters may be of benefit in reduction of dietary carbonyl substances, analogous to the proposed action of other non-absorbable agents described herein. Such derivatives of sucrose polyesters would include structures in which the carbonyl trapping functional group is in the ω-, ω-1 or other isomeric position(s) within the fatty acyl chains, fatty acyl chains having more than one nitrogen functional group and fatty acyl chains having hydroxyl groups. Such aminated sucrose polyesters may be used in pure form as a dietary supplement, or may be prepared as a coating on a particulate carrier such as cellulose or styrene divinylbenzene copolymer resin.

(c). Synthetic Polyamine Polymers (c)(1). Synthetic polysaccharides consisting partly or entirely of aminosugars bound by β-1,2-β-1,3, β-1,4 and/or β-1,6 linkages may be regarded as non-absorbable potential carbonyl trapping agents.

(c)(2). Mixed polysaccharide polymeric derivatives. Primary amine, aminoalkyl (one to ten carbons per alkyl group), aminohydroxyalkyl (one to ten carbons per alkyl group and one to ten hydroxyl groups per alkyl group), aminoguanidine, aminoguanidinylalkyl (one to ten carbons per alkyl group), aminoalkylguanidinyl (one to ten carbons per alkyl group), guanidine, aminobenzene and aminoalkylbenzene (one to ten carbons per alkyl group) functional groups may be covalently attached to matrices such as epi-chloro-hydrin copolymers of cellulose or chitin. Functional group spacer groups may include alkene as well as alkyl groups.

(c)(3). Non-polysaccharide polymeric derivatives. Primary amine, aminoalkyl (one to ten carbons per alkyl group), aminohydroxyalkyl (one to ten carbons per alkyl group and one to ten hydroxyl groups per alkyl group), aminoguanidine, aminoguanidinylalkyl (one to ten carbons per alkyl group), aminoalkylguanidinyl (one to ten carbons per alkyl group), guanidine, aminobenzene and aminoalkylbenzene (one to ten carbons per alkyl group) functional groups may be covalently attached to a wide variety of synthetic non-digestible polymers. Functional group spacer groups may include alkene as well as alkyl groups. Like their sugar-based counterparts, these agents should be capable of reacting with dietary carbonyl compounds. Nitrogen-containing functional groups may be covalently attached to synthetic supports such as polystyrene, styrene-divinylbenzene copolymer, polyvinyl alcohol and crosslinked derivatives thereof.

6. Administration of a Closed Group of Antioxidant Co-Agents

For purposes of the present invention the category of antioxidant co-agents, vitamin co-agents, co-agents which are metabolites at risk of depletion, sulfhydryl substance co-agents, and co-agents which may facilitate glutathione activity, it is assumed herein that these substances are administered orally unless stated otherwise. Dosage ranges for these co-agents refer to human use and may be adjusted accordingly for use by other mammals on a per kilogram basis. It is claimed herein that the therapeutic value of the primary agents described above can be maximized by administration in conjunction with recognized antioxidant free radical trapping compounds such as α-tocopherol [Ferrari et al. *Am. J. Med.* 91(Suppl 3C):95S–105S (1991); Stuckey in *CRC Handbook of Food Additives*, Furia, T E, ed. (West Palm Beach, Fla., CRC Press, 1968) pp. 214–215], dosage range from 100 I. U. daily to 3,500 I. U. daily, or other co-agents previously recognized as adjunts which facilitate in vivo capability to inhibit lipid peroxidation. The dosage range noted above for α-tocopherol is also claimed for other vitamin E derivatives such as β-tocopherol, γ-tocopherol, δ-tocopherol, ε-tocopherol, $\zeta_1$-tocopherol, $\zeta_2$-tocopherol and η-tocopherol, as well as pharmaceutically acceptable ester derivatives thereof such as the corresponding acetate, succinate and nicotinate forms.

Citric acid, dosage range from 200 mg daily to 20 gm daily, may be included in this catagory of co-administered agents, as it is recognized as having antioxidant properties [Budavari et al. *Merck Index,* 11th ed. (Rahway, N.J., Merck & Co., 1989) pg. 363]. Alternatively, this co-agent may be consumed as a combination of potassium citrate monohydrate and citric acid monohydrate in a weight ratio of 3.3 to 1, or other weight ratio selected so as to alkalinize a composition. Citric acid is also recognized as an inhibitor of Maillard reactions [Stuckey in *CRC Handbook of Food Additives*, Furia, T E, ed. (West Palm Beach, Fla., CRC Press, 1968) pg. 210].

In a published list of agents which function to supplement the chain-breaking antioxidant property of vitamin E, Tappel [*Am. J. Clin. Nutr.* 23:1137–1139 (1970)] mentioned ubiquinol, seleno-amino acids and sulfhydryl compounds (e.g., glutathione, sulfhydryl proteins, cysteine and methionine). An intravenous, intramuscular, subcutaneous or oral dosage range from 10 mg daily to 500 mg daily for the class of ubiquinols, coenzyme $Q_n$, where n=1–12, is proposed herein. An intravenous, intramuscular, subcutaneous or oral dosage range from 10 mg daily to 500 mg daily for glutathione is proposed herein.

Other substances in this general group include:

butylated hydroxytoluene, dosage range from 10 mg daily to 1 gm daily;

butylated hydroxyanisole, dosage range from 5 mg daily to 40 mg daily;

propyl gallate, dosage range from 10 mg daily to 1 gm daily;

dodecylgallate, dosage range from 10 mg daily to 1 gm daily;

tert-butylhydroquinone, dosage range from 10 mg daily to 1 gm daily;

dihydrolipoic acid, intravenous, intramuscular, subcutaneous or oral dosage range from 10 mg daily to 500 mg daily;

prostaglandin $B_1$ oligomers (also known as polymeric 15-keto prostaglandin B or $PGB_x$), intravenous, intramuscular, subcutaneous or oral dosage range from 5 mg/kg daily to 400 mg/kg daily;

2-aminomethyl-4-tert-butyl-6-iodophenol, dosage range from 0.5 mg/kg daily to 600 mg/kg daily;

2-aminomethyl-4-tert-butyl-6-propionylphenol, dosage range from 20 mg/kg daily to 500 mg/kg daily;

2,6-di-tert-butyl-4-[2'-thenoyl]phenol, dosage range from 3 mg/kg daily to 300 mg/kg daily;

N,N'-diphenyl-p-phenylenediamine, dosage range from 5 mg/kg daily to 500 mg/kg daily;

ethoxyquin, dosage range from 5 mg/kg daily to 500 mg/kg daily;

probucol, dosage range from 25 mg daily to 1 gm daily;

ebselen, intravenous, intramuscular, subcutaneous or oral dosage range from 5 mg/kg daily to 500 mg/kg daily;

5-[[3,5-bis(1,1-dimethylethyl)-4-hydroxyphen-yl] methylene]-3-(dimethylamino)-4-thiazolidinone (LY221068), dosage range from 1 mg/kg daily to 100 mg/kg daily;

5-[[3,5-bis(1,1-dimethylethyl)-4-hydroxyphenyl]methylene]-3-(methylamino)-4-thiazolidinone (LY269415), dosage range from 1 mg/kg daily to 100 mg/kg daily;

D-myoinositol-1.2.6-trisphosphate, intravenous, intramuscular, subcutaneous or oral dosage range from 10 mg/kg daily to 1.5 gm/kg daily;

nordihydroguaiaretic acid, intravenous, intramuscular, subcutaneous or oral dosage range from 100 mg/kg daily to 2 gm/kg daily;

deferoxamine mesylate, intravenous, intramuscular or subcutaneous dosage range from 100 mg daily to 2 gm daily;

tirilazad mesylate (U-74006F), intravenous, intramuscular or subcutaneous dosage range from 150 μg/kg/hr to 15 mg/kg/hr;

derivative of tirilazad in which the steroid portion of the chemical structure has been replaced with the tetramethyl chroman portion of d-α-tocopherol (U78517F), intravenous, intravenous or subcutaneous dosage range from 150 μg/kg/hr to 15 mg/kg/hr;

trimetazidine, dosage range from 100 μpg/kg daily to 3.0 mg/kg daily;

N,N'-dimethylthiourea, intravenous, intramuscular, subcutaneous or oral dosage range from 5 mg/kg daily to 100 mg/kg daily;

2-(2-hydroxy-4-methylphenyl) aminothiazolehydrochloride, dosage range from 0.1 mg/kg daily to 50 mg/kg daily; and 2-L-oxothiazolidine, dosage range from 5 mg/kg daily to 500 mg/kg daily.

Thioctic acid, also known as α-lipoic acid, is also included in this category in a dosage range from 10 mg daily to 500 mg daily, including its sodium salt and ethylenediamine derivatives. This agent, a recognized growth factor [Budavari et al. *Merck Index,* 11th ed. (Rahway, N.J., Merck & Co., 1989) pg. 1469] and antioxidant [Stoll et al. *Ann. NY Acad. Sci.* 717:122–128 (1994)], may tend to be depleted in the tissues of patients having a dysfunction of aldehyde and/or ketone metabolism. The ability of acetaldehyde to combine with thioctic acid, thus deactivating it, has been reported [Smith in *Greenfield's Neurology*, Blackwood, W and Corsellis, JAN, eds. (Chicago, Year Book Medical Publishers, 1976) pg. 195]. Selenium and pharmaceutically acceptable salts thereof are also be included herein, dosage range from 25 μg daily to 0.5 mg daily, as selenium has recognized indirect antioxidant properties [Stuckey in *CRC Handbook of Food Additives*, Furia, T E, ed. (West Palm Beach, Fla., CRC Press, 1968) pg. 236]. For similar reasons, zinc and pharmaceutically acceptable salts thereof should also be included in this catagory, dosage range from 5 mg daily to 400 mg daily.

Additional antioxidants and free radical trapping substances have been recognized as plant (e.g., vegetable) active ingredients. This category, also claimed herein, includes parthenolide, dosage range from 10 mg daily to 1 gm daily; lycopene, dosage range from 10 mg daily to 1 gm daily; daidzin, dosage range from 10 mg daily to 1 gm daily; genistein, dosage range from 10 mg daily to 1 gm daily; quercetin, dosage range from 10 mg daily to 1 gm daily; morin, dosage range from 10 mg daily to 1 gm daily; curcumin, dosage range from 10 mg daily to 1 gm daily; apigenin, dosage range from 10 mg daily to 1 gm daily; sesamol, dosage range from 10 mg daily to 1 gm daily; chlorogenic acid, dosage range from 10 mg daily to 1 gm daily; fisetin, dosage range from 10 mg daily to 1 gm daily; ellagic acid, dosage range from 10 mg daily to 1 gm daily; quillaia saponin, dosage range from 10 mg daily to 1 gm daily; capsaicin, dosage range from 10 mg daily to 1 gm daily; ginsenoside, dosage range from 10 mg daily to 1 gm daily; silymarin, dosage range from 10 mg daily to 1 gm daily; kaempferol, dosage range from 10 mg daily to 1 gm daily; ginkgetin, dosage range from 10 mg daily to 1 gm daily; bilobetin, dosage range from 10 mg daily to 1 gm daily; isoginkgetin, dosage range from 10 mg daily to 1 gm daily; isorhamnetin, dosage range from 10 mg daily to 1 gm daily; herbimycin, dosage range from 10 mg daily to 1 gm daily; rutin, dosage range from 10 mg daily to 1 gm daily; bromelain, dosage range from 10 mg daily to 1 gm daily; levendustin A, dosage range from 10 mg daily to 1 gm daily; and erbstatin, dosage range from 10 mg daily to 1 gm daily.

For the purposes of this invention, dimethyl sulfoxide is exempted from inclusion in this category of co-agent or any other category of co-agent herein.

7. Administration of a Closed Group of Vitamin Co-Agents

It is yet still another object of this invention that the safety and effectiveness of the products described herein may be optimized by co-administration of vitamins which may be inadvertently depleted by the treatment or which may otherwise contribute to the clinical effectiveness of the compositions. This group includes:

retinol, dermal, subcutaneous, intravenous, intramuscular or oral dosage range from 10 μg/kg daily to 1 mg/kg daily;

vitamin A aldehyde (retinal), dermal, subcutaneous, intravenous, intramuscular or oral dosage range from 10 μg/kg daily to 1 mg/kg daily;

vitamin A acid (retinoic acid), dermal, subcutaneous, intravenous, intramuscular or oral dosage range from 10 μg/kg daily to 1 mg/kg daily;

retinyl acetate, dermal, subcutaneous, intravenous, intramuscular or oral dosage range from 10 μg/kg daily to 1 mg/kg daily;

vitamin $B_1$ (thiamine HCl), dosage range from 1 mg daily to 1.5 gm daily;

thiamine propyl disulfide, dosage range from 1 mg daily to 1.5 gm daily;

thiamine disulfide, dosage range from 1 mg daily to 1.5 gm daily;

thiamine disulfide O,O-diisobutyrate, dosage range from 1 mg daily to 1.5 gm daily;

thiamine disulfide hydrochloride, dosage range from 1 mg daily to 1.5 gm daily;

thiamine disulfide phosphate, dosage range from 1 mg daily to 1.5 gm daily;

thiamine mononitrate, dosage range from 1 mg daily to 1.5 gm daily;

thiamine 1,5-salt, dosage range from 1 mg daily to 1.5 gm daily;

thiamine phosphoric acid ester chloride, dosage range from 1 mg daily to 1.5 gm daily;

thiamine phosphoric acid ester phosphate salt, dosage range from 1 mg daily to 1.5 gm daily;

thiamine triphosphoric acid ester, dosage range from 1 mg daily to 1.5 gm daily;

vitamin $B_2$ (riboflavin), dosage range from 1 mg daily to 1 gm daily;

riboflavin tetrabutyrate, dosage range from 1 mg daily to 1 gm daily;

riboflavine 5'-phosphate ester monosodium salt, dosage range from 1 mg daily to 1 gm daily;

vitamin $B_5$ (pantothenic acid), dosage range of from 5 mg daily to 2 gm daily;

pantothenic acid sodium salt, dosage range of from 5 mg daily to 2 gm daily;

pantothenic acid calcium salt, dosage range of from 5 mg daily to 2 gm daily;

vitamin $B_6$ (pyridoxine HCl), dosage range from 10 mg daily to 1.75 gm daily;

pyridoxal, dosage range from 10 mg daily to 1.75 gm daily;

pyridoxal HCl, dosage range from 10 mg daily to 1.75 gm daily;

pyridoxal 5-phosphate, dosage range from 10 mg daily to 1.75 gm daily;

pyridoxal 5-phosphate calcium salt, dosage range from 10 mg daily to 1.75 gm daily;

pyridoxamine, dosage range from 10 mg daily to 1.75 gm daily;

pyridoxamine dihydrochloride, dosage range from 10 mg daily to 1.75 gm daily;

pyridoxamine phosphate, dosage range from 10 mg daily to 1.75 gm daily;

vitamin $B_{12}$ (cyanocobalamin), intravenous or oral dosage range from 1 μg daily to 1 mg daily;

methyl vitamin $B_{12}$ (co-methylcobalamin), intravenous or oral dosage range from 1 μg daily to 1 mg daily;

vitamin $D_2$, dosage range from 400 units daily to 40,000 units daily;

vitamin $D_3$, dosage range from 400 units daily to 40,000 units daily;

vitamin $D_4$, dosage range from 400 units daily to 40,000 units daily;

vitamin H (biotin), intravenous, subcutaneous or oral dosage range from 150 μg daily to 200 mg daily;

vitamin $K_1$ (phytonadione), intravenous, subcutaneous or oral dosage range from 100 μg daily to 100 mg daily;

diacetyl dihydro vitamin $K_1$, intravenous, subcutaneous or oral dosage range from 100 μg daily to 100 mg daily;

vitamin $K_1$ oxide, intravenous, subcutaneous or oral dosage range from 100 μg daily to 100 mg daily;

vitamin(s) $K_2$ (menaquinones), intravenous, subcutaneous or oral dosage range from 100 μg daily to 100 mg;

vitamin $K_{2(35)}$, intravenous, subcutaneous or oral dosage range from 100 μg daily 100 mg daily;

vitamin $K_{2(35)}$ dihydrodiacetate, intravenous, subcutaneous or oral dosage range from 100 μg daily to 100 mg daily;

vitamin $K_{2(30)}$, intravenous, subcutaneous or oral dosage range from 100 μg daily to 100 mg daily;

vitamin $K_{2(30)}$ dihydrodiacetate, intravenous, subcutaneous or oral dosage range from 100 μg daily to 100 mg daily;

vitamin $K_5$, intravenous, subcutaneous or oral dosage range from 100 μg daily to 100 mg daily;

vitamin $K_5$ hydrochloride, intravenous, subcutaneous or oral dosage range from 100 μg daily to 100 mg daily;

N-acetyl vitamin $K_5$, intravenous, subcutaneous or oral dosage range from 100 μg daily to 100 mg daily;

vitamin $K_6$, intravenous, subcutaneous or oral dosage range from 100 μg daily to 100 mg daily;

vitamin $K_6$ dihydrochloride, intravenous, subcutaneous or oral dosage range from 100 μg daily to 100 mg daily;

vitamin $K_7$, intravenous, subcutaneous or oral dosage range from 100 μg daily to 100 mg daily;

vitamin $K_7$ hydrochloride, intravenous, subcutaneous or oral dosage range from 100 μg daily to 100 mg daily;

vitamin K-S(II), intravenous, subcutaneous or oral dosage range from 100 μg daily to 100 mg daily;

vitamin $L_1$, dosage range from 10 mg daily to 500 mg daily;

vitamin $L_2$, dosage range from 10 mg daily to 500 mg daily;

vitamin U, dosage range from 25 mg daily to 1 gm daily;

methylmethioninesulfonium bromide (bromide analog of vitamin U, dosage range from 25 mg daily to 1 gm daily;

α-carotene, dosage range from 20 mg daily to 300 mg daily;

β-carotene, dosage range from 20 mg daily to 300 mg daily;

γ-carotene, dosage range from 20 mg daily to 300 mg daily;

ω-carotene, dosage range from 20 mg daily to 300 mg daily;

Ψ-,Ψ-carotene (also known as lycopene; Sies, 1991, pg. 33S), dosage range from 5 mg daily to 300 mg daily;

7,7',8,8',11,12-hexahydro-Ψ-,Ψ-carotene (also known as phytofluene; Halliwell, 1991, pg. 576), dosage range from 5 mg daily to 300 mg daily;

L-carnitine (vitamin $B_T$; Carnitor, Sigma-Tau Pharmaceuticals), dosage range from 100 mg daily to 3 gm daily;

acetyl-L-carnitine, dosage range from 100 mg daily to 3 gm daily;

folic acid (vitamin Bc), dosage range from 0.5 mg daily to 50 mg daily;

folinic acid, dosage range from 0.5 mg daily to 50 mg daily;

folinic acid calcium salt pentahydrate, dosage range from 0.5 mg daily to 50 mg daily;

niacinamide, dosage range from 100 mg daily to 10 gm daily;

nicotinic acid (vitamin $B_3$; Nicolar, Rhone-Poulenc Rorer), dosage range from 100 mg daily to 10 gm daily;

nicotinic acid sodium salt sesquihydrate, dosage range from 100 mg daily to 10 gm daily; and nicotinic acid monoethanolamine salt, dosage range from 100 mg daily to 10 gm daily.

Several of these vitamins possess carbonyl functional groups and thus may be depleted by clinical use of the present invention. Others have a reported antioxidant effect, such as the carotenes, or may possess an anti-inflammatory effect, such as carnitine [Elliott et al. *Agents Actions* 32:88–89 (1991)], retinoic acid [Fumarulo et al. *Agents Actions* 34:339–344 (1991)] and retinyl acetate [Fumarulo et al. (1991)].

8. Administration of a Closed Group of Co-Agent Metabolites at Risk of Depletion It is another object of this invention that the safety and effectiveness of the products described herein may be optimized by co-administration of other metabolites, such as glycine, which may be depleted within the body during long term use of the primary agents of the present disclosure. Use of glycine within the dosage range of from 1 gm daily to 20 gm daily is claimed herein. As many of the absorbable amine drugs of the category of primary agents described herein are excreted from the body as glycine conjugates, co-administration of glycine may be advisable. For purposes of the present invention, this group of co-agents shall also be defined as including the pharmaceutically acceptable salts, such as the hydrochloride, hemihydrochloride and sodium salts.

9. Administration of a Closed Group of Sulfhydryl Substance Co-Agents

Noting the well documented ability of carbonyl agents to react with sulfhydryl groups [Jellum et al. *Clin. Chim. Acta* 47:191–201 (1973)], it is a further object of this invention that L-methionine, dosage range from 200 mg daily to 4 gm daily and homocysteine, dosage range from 200 mg daily to 2 gm daily may also be of clinical benefit as absorbable drugs capable of covalently binding aldehyde or ketone agents. Homocysteine contains a free sulfhydryl group. Likewise, acetyl-homocysteine thiolactone, intravenous, intramuscular, subcutaneous or oral dosage range from 0.5 mg/kg daily to 25 mg/kg daily may also be included in this group. Methionine is converted in vivo to homocysteine by several enzymatic reactions which remove a methyl group. L-Methionine also has a demonstrated ability to scavenge hypochlorous acid, a reactive oxygen specie [Saari et al. *Inflammation* 17: 403–415 (1993)].

10. Administration of a Closed Group of Co-Agents Consisting of Substances Which May Facilitate Glutathione Activity In addition, the present invention includes use of various co-agents which may facilitate glutathione activity. Use of N-acetyl-cysteine [Dansette et al. in *Antioxidants in Therapy and Preventive Medicine*, Emerit, I, sr. ed. (New York, Plenum Press, 1990) pp. 209–215], dosage range from 10 mg/kg daily to 150 mg/kg daily, has been reported to increase the levels of plasma cysteine, plasma glutathione and red blood cell glutathione [Bernard *Am. J. Med.* 91(Suppl 3C):54S–59S (1991)], and to induce a 100-fold increase in myocardial glutathione subsequent to experimental ischemia and reperfusion [Ferrari et al. *Am. J. Med.* 91(Suppl 3C):95S–105S (1991)]. N-Acetylcysteine reacts with hypochlorous acid, $HO^-$ and $H_2O_2$ [Bernard (1991)], as well as with reactive aldehydes found in tobacco smoke [Ohman et al. *Agents Actions* 36:271–277 (1992)]. Other substances in this class include L-2-oxothiazolidine-4-carboxylic acid, reported to hydrolyse in vivo to cysteine [Halliwell *Drugs* 42:569–605 (1991) pg. 590], dosage range from 0.3 mmol/kg daily to 3 mmol/kg daily; timonacic, also known as 4-thiazolidinecarboxylic acid [Dansette et al. in *Antioxidants in Therapy and Preventive Medicine*, Emerit, I, sr. ed. (New York, Plenum Press, 1990) pp. 209–215], dosage range from 10 mg daily to 500 mg daily; cysteamine [Dansette et al. (1990)], dosage range from 200 mg daily to 4 gm daily; lipoamide derivatives [Dansette et al. (1990)] such as malotilate (Kantec), dosage range from 100 mg daily to 2 gm daily; sulfarlem [ADT; Dansette et al. (1990)], intravenous, intramuscular, subcutaneous or oral dosage range from 100 mg/kg daily to 1 gm/kg daily; and oltipraz [Dansette et al. (1990)], intravenous, intramuscular, subcutaneous or oral dosage range from 100 mg/kg daily to 1 gm/kg daily, as these co-agents may further serve to improve the invention described in U.S. patent application Ser. No. 08/026,617.

11. Administration of a Closed Group of Pharmaceutically Acceptable Carriers Suitable for the Orally Administered Component of a Composition of the Present Invention It is further disclosed herein that the methods of the present invention can include the incorporation of one or more pharmaceutically acceptable carrier suitable for the orally administered component thereof selected from the group consisting of carboxymethyl cellulose, microcrystalline cellulose, cellulose, starch, dicalcium phosphate, tricalcium phosphate, stearic acid, magnesium stearate, silica, soy flour, watercress, yeast, alfalfa, parseley, lecithin, rice bran, gum tragacanth, gum guar, gum agar, gum arabic, gum carrageenan, gum ghatti, gum karaya, locust bean gum, gum mastic, gum mesquite and gum xanthan, wherein said pharmaceutically acceptable carrier suitable for the orally administered component thereof may be compounded together with a primary agent or a primary agent in combination with at least one co-agent. Said incorporation of one or more pharmaceutically acceptable carrier suitable for the orally administered component thereof may contribute to the the overall utility of the composition, for example, as a factor in determining the rate at which the composition will dissolve subsequent to oral administration.

12. Factors Affecting Daily Dosage Schedule

A daily protocol of primary agent drug consumption, in combination with co-agents defined herein, may be defined such that drug products are administered in timed-release and/or color coded tablets or capsules, so as to facilitate patient compliance and maximize therapeutic value. Alternatively, a therapeutic composition may be incorporated into a foodstuff product, so as to encourage regular, long term patient compliance.

13. Example of the Invention of U.S. patent application Ser. No. 08/026,617 Used in a Clinical Trial: Use of PABA in Combination with Antioxidant and Vitamin Co-Agents Therapeutic Protocol Subject 1 is a male individual born in 1948 and having hereditary motor and sensory neuropathy. The subject's family has the X-linked subvariety of the disease. All of the composition ingredients of this example were administered via the oral route.

On Sep. 1, 1990 Subject 1 began taking three 100 mg tablets of p-aminobenzoic acid per day. This daily dosage consisted of single 100 mg tablets (Schiff Products, Moonachie, N.J.) taken one at a time approximately every eight hours. Also initiated at this time and taken three times per day: DL-methionine, 500 mg and vitamin E (as mix tocopherols in oil-based capsules), 200 I.U. His weight at the time was approximately 165 lbs. The daily dosage times were approximately 8:00 AM, 4:00 PM and 11:30 PM. This original low dosage of PABA was selected in part as a check to ensure no adverse immunologic reaction. Symptoms of allergic reaction such as bronchial constriction or skin rash were not observed. Actually, no clinical reaction to PABA was observed.

On Oct. 1, 1990 Subject 1 began taking a total of 600 mg PABA per day by doubling the original dosage noted above; 200 mg taken three times per day. Also taken with PABA: DL-methionine, 500 mg and vitamin E, 200 I.U.

On Jan. 1, 1991 Subject 1 began taking three 550 mg capsules of PABA (Solgar Co., Lynbrook, N.Y.) per day, one approximately every eight hours. DL-Methionine use was doubled to 1,000 mg every eight hours. Likewise, vitamin E deosage was doubled to 400 I.U. every eight hours. In addition, the following dietary supplements were initiated and taken once per day (4:00 PM):

pantothenic acid, 250 mg;
β-carotene, 25,000 I.U.;
selenium (Osco, Oak Brook, Ill.), 50 ug;
vitamin $B_1$, 100 mg;
and one Osco brand "balanced B complex 50" tablet, each tablet consisting of:

| folic acid | 100 ug | vitamin $B_1$ | 50 mg |
| vitamin $B_2$ | 50 mg | niacin | 50 mg |
| vitamin $B_6$ | 50 mg | vitamin $B_{12}$ | 50 ug |
| biotin | 50 ug | pantothenic acid | 50 mg |

The ingredients as listed on the label are: "dicalcium phosphate, d-calcium pantothenate, pyridoxine hydrochloride, hydrogenated cottonseed oil, cellulose, niacinamide, rifoflavin, thiamine mono-nitrtate, stearic acid, modified cellulose gum, magnesium stearate, silica, resin, gum acacia, hydroxypropylcellulose, rice bran, yeast, para-aminobenzoic acid, alfalfa, watercress, parsley, lecithin, cyanocobalamin, folic acid, biotin." Except as noted above, the amounts of ingredients (such as PABA) were not stated.

On Feb. 24, 1991 Subject 1 began taking six 550 mg capsules of PABA per day, two every eight hours plus the dietary supplement combination initiated January 1st. DL-Methionine and vitamin E dosage were continued as initiated January 1st; 3,000 mg and 1,200 I.U. total daily, respectively. Dosage of additional dietary supplements was also continued as initiated January 1st, with the addition of 100 mg vitamin $B_1$ per day. Also, selenium daily dosage was reduced to 12 ug per day.

As of May 1, 1991 consumption of pantothenic acid and vitamin $B_1$ were tripled to 250 mg 3× daily and 100 mg 3× daily, respectively, taken with PABA. Also initiated now, vitamin $B_6$, 100 mg taken 3× daily with PABA.

As of Jul. 1, 1991 the methionine product was switched to "L-Methionine 500 mg Caps with Vitamin $B_6$" (Nature's Plus, Farmingdale, N.Y.). Each capsule has the free form of the L-amino acid and 50 mg vitamin $B_6$. This dose of vitamin $B_6$ is in addition to the 300 mg/day noted in the preceding paragraph.

As of Jul. 26, 1991 the vitamin E product was switched to "Natural Dry All E, 400 I.U." (Schiff Products, Moonachie, N.J.). One of these dry powder capsules is taken 3× daily with PABA, as before.

As of Aug. 7, 1991 daily doses of PABA, methionine and vitamin E were increased by 50%. Thus starting at this time, three 550 mg PABA capsules, three 500 mg methionine capsules, one 400 I.U. dry vitamin E and a 200 I.U. dry vitamin E capsule were taken at a time, three times per day. Daily totals of these agents were now: PABA, 4.95 gm; methionine, 4.5 gm; and vitamin E, 1,800 I.U. Other agents were taken as before.

As of Nov. 22, 1991 the daily dose of PABA was increased. Thus starting at this time, four 550 mg PABA capsules were taken at a time, three times per day. Daily total of PABA was now 6.6 gm. Other agents were taken as before.

Nerve Conduction Studies on Subject 1

On Jun. 20, 1988 Subject 1 participated in a nerve conduction research study at the National Institutes of Health. Nerve conduction data was recorded from the left median and ulnar nerves, which included conduction velocity, amplitude and distal latency for each nerve. On May 6, 1992 Subject 1 was tested again at the office of a neurologist in Bryn Mawr, Pa. The results of these studies may be summarized as follows.

| | Conduction velocity meters/sec | Amplitude mV | Latency msec |
| --- | --- | --- | --- |
| Median Nerve | | | |
| Jun. 20, 1988 study | 28 | 0.4 | 12.4 |
| May 6, 1992 study | 28.2 | 0.4 | 13.1 |
| Ulnar Nerve | | | |
| Jun. 20, 1988 study | 29 | 1.3 | 13.8 |
| May 6, 1992 study | 31.8 | 2.4 | 13.1 |

These data indicate that there was little change in the neurophysiological status of the left median nerve during the course of the experimental therapeutic drug trial; conduction velocity and amplitude remained unchanged, while the distal latency increased (that is, worsened) by six percent. However, data on the left ulnar nerve document an improvement in neurophysiological status; conduction velocity improved by ten percent, amplitude improved by eighty-five percent and distal latency improved by five percent.

This experimental drug trial involved a step-by-step increase in dosages over an extended period. Dosages of PABA, the primary agent were slowly increased from September, 1990 to November, 1991. The final PABA dosage level (6.6 gm/day) was maintained from November, 1991 to May, 1992, a period of approximately six and one half months. During this study period the left ulnar nerve, which was more intact to begin with, began to show improvement in neurophysiological status. This slow improvement in nerve conduction status is in accord with what is known of the ability of peripheral nerves to regenerate axons. As Bradley [*Muscle & Nerve* 13:833–842 (1990)] has noted:

... it may take as long as 18 months before regenerating axons reach the distal denervated muscles where the site of the lesion lay in proximal nerve roots or plexuses. In neuronopathies, where cell death has occurred, any degree of recovery can only occur by peripheral sprouting from axons of surviving neurons. This also appears to be a relatively slow process. Hence, therapeutic trials must extend for long enough to ensure that the slow biological reparative processes can be detected.

The available findings on the left ulnar nerve of Subject 1 indicate that conduction velocity has improved, the number of detectable axonal fibers has almost doubled (improved amplitude) and a modest increase in re-innervation of the distal muscle group has begun to occur (improved latency).

14. Use of the Primary Agents and Categories of Co-Agents of the Present Invention to Treat Subject Diseases As summarized above, it is evident that presently available pharmaceutical technology for treatment of the diseases addressed herein is almost entirely symptomatic, as well as temporary and of partial clinical benefit, at best. The dosages of any of the medicaments effective to treat the underlying diseases discussed herein, except those which are still the subjects of preliminary laboratory studies, are well known to those skilled in the art. Significant adverse side effects accompany many of these treatments, which limit their use. The present invention defines the use of previously recognized technology in combination with the invention originally described in U.S. patent application Ser. No. 07/660,561, so as to achieve greater clinical effectiveness in treatment of these diseases. In using the therapeutic technology defined herein, physicians may achieve in some cases the clinical benefits of previously recognized drugs while using lower dosage levels, thus minimizing adverse side effects. Within the context of the present invention, it is important to note the documentation provided by Flood et al. [*Life Sci.* 42:2145–2154 (1988)]. Their findings indicate that when drugs are used in combination they may provide beneficial effect at reduced dosages which are ineffective when drugs are administered alone. This approach may permit wider and more effective use of previously recognized drug technology. It is acknowledged herein that for many of the medicaments effective to treat the underlying diseases the optimum dosage must be determined on an individualized basis, and may be below or above the dosage range generally recognized for public use. It is to be understood that in particular cases it will be desirable to go beyond the dosage ranges noted below. Except where stated otherwise, the drugs listed in the following examples are to be administered orally.

EXAMPLE 1

Clinical treatment of Parkinson's disease can be improved by use of at least one primary agent of the present invention as disclosed in section (3), optionally in combination with one or more substances selected from sections (5) through (10), inclusive, and optionally in combination with one or more co-agent medicament to treat the disease or a symptom thereof, said medicament including co-agent use of:

(a) carbidopa and levodopa compositions (Sinemet tablets and Sinemet CR controlled release tablets, Du Pont Pharmaceuticals), dosage range from 30 mg carbidopa and 300 mg levodopa daily to 600 mg carbidopa and 2,400 mg levodopa daily;

(b) dopamine agonists such as bromocriptine mesylate (Parlodel SnapTabs and capsules, Sandoz Pharmaceuticals), dosage range from 1.25 to 140 mg daily;

pergolide mesylate (Permaxm, Lilly), dosage range from 0.05 mg daily to 5 mg daily;

(+)-4-propyl-9-hydroxynaphthoxazine, dosage range from 1 ug/kg/day to 0.3 mg/kg/day;

apomorphine, dosage range from 0.1 mg/kg/day to 2 mg/kg/day; and ciladopa, dosage range from 0.5 mg/kg/day to 20 mg/kg/day;

(c) anticholinergic medications such as benztropine mesylate (Cogentin, Merck & Co.), dosage range from 0.5 mg daily to 6 mg daily; and biperiden, dosage range from 0.5 mg daily to 6 mg daily;

(d) antihistamines such as orphenadrine citrate (Norflex sustained-release tablets, Norgesic tablets and Norgesic Forte tablets, 3M Pharmaceuticals), dosage range from 100 mg daily to 200 mg daily;

(e) tricyclic antidepressants such as amitriptyline HCl (Elavil, Stuart), dosage range from 50 mg daily to 300 mg daily;

amitriptyline HCl/perphenazine combinations (Etrafon, Schering), dosage range from 4 mg perphenazine and 50 mg amitriptyline daily to 16 mg perphenazine and 100 mg amitriptyline daily;

amitriptyline/chlordiazepoxide combinations (Limbitrol, Roche Products), dosage range from 5 mg chlordiazepoxide and 12.5 mg amitriptyline daily to 60 mg chlordiazepoxide and 150 mg amitriptyline daily;

nortriptyline HCl (Pamelor, Sandoz Pharmaceutical), dosage range from 25 mg daily to 150 mg daily;

imipramine, dosage range from 2 mg daily to 150 mg daily; and doxepin, dosage range from 2 mg daily to 150 mg daily;

(f) serotonin reuptake inhibitor antidepressants such as fluoxetine HCl (Prozac, Dista), dosage range from 20 mg daily to 80 mg daily; and sertraline (Zoloft, Pratt Pharmaceuticals), dosage range from 50 mg daily to 200 mg daily;

(g) β blocker agents such as propranolol HCl (Inderal, Wyeth-Ayerst Laboratories), dosage range from 30 mg daily to 640 mg daily;

pindolol (Visken, Sandoz Pharmaceuticals), dosage range from 10 mg daily to 60 mg daily;

metoprolol tartrate (Lopressor, Geigy), dosage range from 100 mg daily to 450 mg daily;

metoprolol succinate (Toprol XL, Astra), dosage range from 50 mg daily to 400 mg daily; and atenolol (Tenormin, ICI Pharma), dosage range from 50 mg daily to 200 mg daily;

(h) selegiline (Eldepryl, Somerset), dosage range from 5 mg daily to 10 mg daily;

(i) selegiline in combination with tocopherol, dosage range from 5 mg selegiline and 500 I. U. tocopherol daily to 10 mg selegiline and 3500 I. U. tocopherol daily;

(j) D-cycloserine with or without a cholinesterase inhibitor co-agent, dosage range from 0.1 mg/kg daily to 15 mg/kg daily;

(k) neurotransmission enhancer drugs such as lisuride, dosage range from 0.1 mg daily to 2 mg daily;

(l) peripheral decarboxylase inhibitors other than carbidopa such as benserazide used in combination with levodopa, dosage range from 25 mg benserazide and 500 mg levodopa daily to 200 mg benserazide and 2,400 mg levodopa daily;

(m) N-methyl-D-aspartate glutamate receptor antagonists administered orally, intramuscularly, subcutaneously or intraveneously such as trihexyphenidyl (Artane, Lederle), dosage range from 0.1 mg daily to 20 mg daily;

ethopropazine (Paridol), dosage range from 10 mg daily to 400 mg daily;

procyclidine (Kemadrin, Burroughs Wellcome), dosage range from 1 mg daily to 40 mg daily;

diphenhydramine (Benadryl, Parke-Davis), dosage range from 5 mg daily to 200 mg daily;

dizocilpine (Neurogard, Merck Sharp & Dohme), dosage range from 0.1 ug/kg daily to 10 mg/kg daily;

amantadine (Symmetrel, Du Pont Multi-Source Products), dosage range from 10 mg daily to 400 mg daily;

memantine, dosage range from 10 mg daily to 400 mg daily; and milacemide, dosage range from 50 mg daily to 2.5 grams daily;

(n) tacrine (Cognex, Warner-Lambert), dosage range from 5 mg daily to 200 mg daily, optionally with phosphatidylcholine co-agent, dosage range from zero to 15 gm daily;

(o) (+/−)-9-amino-1,2,3,4-tetrahydroacridin-1-ol, dosage range from 2 mg daily to 200 mg daily;

(p) lazabemide (Hoffmann-La Roche), dosage range from 10 mg daily to 200 mg daily;

(q) tiapride, dosage range from 1 mg daily to 400 mg daily; and (r) antioxidant agents which may be used in combination such as ascorbic acid, dosage range from 1 mg daily to 60 mg daily; N-acetylcysteine, dosage range from 100 mg daily to 1 gm daily; penicillamine, dosage range from 25 mg daily to 2 gm daily; and cysteamine, dosage range from 200 mg daily to 4 gm daily.

EXAMPLE 2

Clinical treatment of either Alzheimer's presenile dementia Alzheimer's senile dementia can be improved by use of at least one primary agent of the present invention as disclosed in section (3), optionally in combination with one or more substances selected from sections (5) through (10), inclusive, and optionally in combination with one or more co-agent medicament to treat the disease or a symptom thereof, said medicament including co-agent use of:

(a) vasodilator or other nootropic direct brain metabolic enhancer drugs such as idebenone, dosage range from 5 mg/kg daily to 150 mg/kg daily; propentophylline, intravenous, intramuscular, subcutaneous or oral dosage range from 50 mg daily to 3 grams daily;

pentoxifylline, dosage range from 50 mg daily to 3 grams daily;

citicoline, dosage range from 50 mg daily to 5 grams daily;

ebiratide, subcutaneous dosage range from 3 ug/kg daily to 1 mg/kg daily;

vinpocetine (Cavinton, Chemical Works of Gedeon Richter, Ltd.), intravenous, intramuscular, subcutaneous or oral dosage range from
5 mg/kg daily to 300 mg/kg daily;

bromvincamine, dosage range from 25 mg daily to 3 grams daily;

cyclandelate, dosage range from 25 mg daily to 3 grams daily;

isoxsuprene, dosage range from 25 mg daily to 3 grams daily;

nafronyl, dosage range from 25 mg daily to 3 grams daily;

papaverine, dosage range from 25 mg daily to 3 grams daily;

suloctidil, dosage range from 25 mg daily to 3 grams daily;

vinburnine, dosage range from 25 mg daily to 3 grams daily;

vincamine, dosage range from 25 mg daily to 3 grams daily;

vindeburnol, dosage range from 25 mg daily to 3 grams daily;

naloxone, intravenous, intramuscular, subcutaneous or oral dosage range from 5 mg daily to 300 mg daily;

ethyl 5-isopropyloxy-4-methyl-β-carboline-3-carboxylate, intravenous, intramuscular, subcutaneous or oral dosage range from 2 mg/kg daily to 100 mg/kg daily;

N'-methyl-β-carboline-3-carboxamide, intravenous, intramuscular, subcutaneous or oral dosage range from 2 mg/kg daily to 100 mg/kg daily;

methyl 6,7-dimethoxy-4-ethyl-β-carboline-3-carboxylate, intravenous, intramuscular, subcutaneous or oral dosage range from 0.1 mg/kg daily to 10 mg/kg daily;

ethyl 5-methoxy-4-ethyl-β-carboline-3-carboxylate, intravenous, intramuscular, subcutaneous or oral dosage range from 1 mg/kg daily to 30 mg/kg daily;

ifenprodil tartrate, dosage range from 0.5 mg/kg daily to 120 mg/kg daily;

piracetam, dosage range from 1 mg daily to 100 mg daily;

aniracetam, dosage range from 50 mg/kg daily to 1 gram/kg daily;

pyroglutamic acid, intravenous, intramuscular, subcutaneous or oral dosage range from 100 mg/kg daily to 5 grams/kg daily;

tenilsetam, dosage range from 10 mg daily (or alternate day) to 1 gram daily (or alternate day), or from 25 mg once a week to 1 gram once a week;

pramiracetam, dosage range from 50 mg/kg daily to 8 grams/kg daily;

oxiracetam, dosage range from 200 mg daily to 2 grams daily;

rolziracetam, intravenous, intramuscular, subcutaneous or oral dosage range from 1 mg daily to 1 gram daily;

razobazam, intravenous, intramuscular, subcutaneous or oral dosage range from 0.1 mg/kg daily to 25 mg/kg daily;

exifone, intravenous, intramuscular, subcutaneous or oral dosage range from 1 mg daily to 1 gram daily;

rolipram, intravenous, intramuscular, subcutaneous or oral dosage range from 1 mg daily to 1 gram daily;

sabeluzole, dosage range from 2 mg daily to 40 mg daily;

nimodipine (Nimotop, Miles Pharmaceutical), dosage range from 300 mg daily to 3.6 gm daily;

flunarizine, dosage range from 2 mg daily to 100 mg daily;

nicergoline (Sermion), intravenous, intramuscular, subcutaneous or oral dosage range from 6 mg daily to 10 grams daily;

phosphatidylserine, intravenous or oral dosage range from 1 mg/kg daily to 250 mg/kg daily;

etiracetam, dosage range from 50 mg/kg daily to 8 grams/kg daily;

dupracetam, intravenous, intramuscular, subcutaneous or oral dosage range from 1 mg daily to 1 gram daily; and ergoloid mesylates (Hydergine, Sandoz Pharmaceuticals), dosage range from 0.5 mg daily to 40 mg daily;

(b) neurotransmission enhancer drugs such as amantadine (Symmetrel, Du Pont Multi-Source Products), dosage range from 10 mg daily to 400 mg daily;

calcium hopantenate, dosage range from 100 mg daily to 4 grams daily;

lisuride, dosage range from 0.1 mg daily to 2 mg daily; and indeloxazine, dosage range from 50 mg daily to 1.5 grams daily;

(c) tiapride, dosage range from 1 mg daily to 400 mg daily;

(d) psychotherapeutic drugs such as haloperidol (Haldol, McNeil Pharmaceutical), dosage range from 0.2 mg daily to 15 mg daily;

bromperidol, dosage range from 20 ug/kg daily to 0.25 mg/kg daily;

thioridazine (Mellaril, Sandoz Pharmaceutical), dosage range from 10 mg daily to 800 mg daily;

thiothixene (Navane, Roerig), dosage range from 2 mg daily to 60 mg daily;

fluphenazine (Prolixin, Apothecon), dosage range from 0.2 mg daily to 40 mg daily;

perphenazine in amitriptyline/perphenazine combinations (Etrafon, Schering), dosage range from 4 mg perphenazine and 50 mg amitriptyline daily to 16 mg perphenazine and 100 mg amitriptyline daily; and molindone (Moban, Du Pont Multi-Source Products), dosage range from 3 mg daily to 225 mg daily;

(e) acetylcholinesterase inhibitors such as physostigmine (Antilirium Injectable, Forest Pharmaceuticals), oral dosage range from 0.1 mg daily to 20 mg daily, or intravenous, intramuscular or subcutaneous dosage range from 5 ug daily to 3 mg daily, optionally with phosphatidylcholine co-agent, oral dosage range from zero to 15 gm daily;

heptylphysostigmine, dosage range from 1 mg daily to 1 gram daily;

donepezil (Aricept, Eisai Company and Pfizer), dosage range from 2 mg daily to 100 mg daily;

tacrine (Coanex, Warner-Lambert), dosage range from 5 mg daily to 200 mg daily, optionally with phosphatidylcholine co-agent, dosage range from zero to 15 gm daily;

(+/−)-9-amino-1,2,3,4-tetrahydroacridin-1-ol, dosage range from 2 mg daily to 200 mg daily;

metrifonate, intramuscular, intravenous, subcutaneous or oral dosage range from 0.1 mg/kg daily to 125 mg/kg daily;

velnacrine (Mentane, Hoechst-Roussel), dosage range from 10 mg daily to 350 mg daily;

phenylmethylsulfonyl fluoride, intravenous, subcutaneous, intramuscular or oral dosage range from 5 mg/kg daily to 60 mg/kg daily;

methanesulfonyl fluoride, intravenous, intramuscular, subcutaneous or oral dosage range from 5 mg/kg daily to 350 mg/kg daily;

huperzine A, intramuscular, intravenous, subcutaneous or oral dosage range from 10 ug/kg daily to 1 mg/kg daily;

huperzine B, intramuscular, intravenous, subcutaneous or oral dosage range from 10 ug/kg daily to 1 mg/kg daily;

edrophonium chloride (Hoffman LaRoche), intravenous, intramuscular, subcutaneous or oral dosage range from 2 mg daily to 400 mg daily;

galanthamine, intravenous, intramuscular, subcutaneous or oral dosage range from 5 mg daily to 100 mg daily; and miotine, intravenous, intramuscular, subcutaneous or oral dosage range from 2 mg daily to 400 mg daily;

(f) calcium channel blocker agents such as diltiazem (Cardizem or Cardizem SR), dosage range from 10 mg daily to 360 mg daily;

verapamil (Calan or Calan SR), dosage range from 10 mg daily to 480 mg daily;

nifedipine (Procardia), dosage range from 3 mg daily to 180 mg daily;

nifedipine (Procardia XL), dosage range from 3 mg daily to 90 mg daily;

nicardipine (Cardene), dosage range from 6 mg daily to 120 mg daily;

isradipine (DynaCirc), dosage range from 0.5 mg daily to 20 mg daily;

amlodipine (Norvasc, Pfizer Labs Division), dosage range from 0.5 mg daily to 10 mg daily; and felodipine (Plendil, Merck & Co.), dosage range from 0.5 mg daily to 20 mg daily;

(g) biogenic amines and agents related thereto such as clonidine (Catapres, Boehringer Ingelheim), dosage range from 0.25 mg daily to 2.4 mg daily;

guanfacine (Tenex, Robins), dosage range from 0.25 mg daily to 3 mg daily;

alaproclate, dosage range from 0.25 mg daily to 3 mg daily;

fipexide, dosage range from 0.25 mg daily to 3 mg daily;

zimeldine, dosage range from 0.25 mg daily to 3 mg daily; and citalopram, dosage range from 0.25 mg daily to 3 mg daily;

(h) antirage drugs such as propranolol (Inderal, Wyeth-Ayerst Laboratories), dosage range from 30 mg daily to 640 mg daily;

carbamazepine (Tegretol, Geigy), dosage range from 40 mg daily to 1.6 gm daily; and fluoxetine (Prozac Pulvules, Dista), dosage range from 20 mg daily to 80 mg daily;

(i) minor tranquilizers such as benzodiazepine agents including diazepam (Valium, Roche Products), dosage range from 0.5 mg daily to 40 mg daily;

lorazepam (Ativan, Wyeth-Ayerst Laboratories), dosage range from 0.5 mg daily to 10 mg daily;

prazepam (Centrax, Parke-Davis), dosage range from 5 mg daily to 60 mg daily;

chlordiazepoxide (Libritabs, Roche Products), dosage range from 5 mg daily to 300 mg daily;

chlordiazepoxide/clidinium combination (Librax, Roche Products), dosage range from 5 mg chlordiazepoxide and 2.5 mg clidinium daily to 20 mg chlordiazepoxide and 10 mg clidinium daily;

chlordiazepoxide/amitriptyline combination (Limbitrol DS, Roche Products), dosage range from 10 mg chlordiazepoxide and 25 mg daily to 60 mg chlordiazepoxide and 150 mg amitriptyline daily;

chlordiazepoxide/esterified estrogen combination (Menrium, Roche Products), dosage range from 5 mg chlordiazepoxide and 0.2 mg esterified estrogen daily to 30 mg chlordiazepoxide and 1.2 mg esterified estrogen daily;

oxazepam (Serax, Wyeth-Ayerst), dosage range from 10 mg daily to 120 mg daily; and clorazepate dipotassium (Tranxene, Abbott Laboratories), dosage range from 3.75 mg daily to 60 mg daily;

(j) angiotensin-converting enzyme inhibitors such as captopril (Capoten, Squibb), dosage range from 5 mg daily to 300 mg daily;

captopril in combination with hydrochlorothiazide (Capozide, Squibb), dosage range from 5 mg captopril and 3 mg hydrochlorothiazide daily to 150 mg captopril and 50 mg hydrochlorothiazide daily;

enalapril maleate (Vasotec, Merck & Co.), dosage range from 0.5 mg daily to 100 mg daily;

enalaprilat, dosage range from 0.5 mg daily to 100 mg daily;

enalapril maleate/hydrochlorothiazide combination (Vaseretic, Merck & Co.), dosage range from 2.5 mg enalapril maleate and 6.25 mg hydrochlorothiazide daily to 20 mg enalapril maleate and 50 mg hydrochlorothiazide daily;

fosinopril (Monopril, Mead Johnson Pharmaceuticals), dosage range from 2 mg daily to 60 mg daily;

lisinopril (Zestril, Stuart), dosage range from 1 mg daily to 40 mg daily;

ramipril (Altace, Hoechst-Roussel), dosage range from 0.5 mg daily to 10 mg daily;

epi-captopril, dosage range from 1 mg daily to 300 mg daily;

alacepril, dosage range from 5 mg daily to 300 mg daily;

quinapril, dosage range from 0.5 mg daily to 40 mg daily;

perindopril, dosage range from 0.2 mg daily to 40 mg daily;

delapril, dosage range from 4 mg daily to 1.5 grams daily;

cilazapril, dosage range from 0.2 mg daily to 40 mg daily;

pivalopril, dosage range from 2 mg daily to 250 mg daily;

rentiapril, dosage range from 1 mg daily to 150 mg daily;

zofenopril, dosage range from 1 mg daily to 150 mg daily; and zofenoprilat, dosage range from 1 mg daily to 150 mg daily;

(k) agents which may enhance acetylcholine synthesis, storage or release such as phosphatidylcholine, dosage range from 1 gm daily to 15 gm daily;

4-aminopyridine, intravenous, intramuscular, subcutaneous or oral dosage range from 0.25 mg/kg daily to 10 mg/kg daily;

3,4-diaminopyridine, intravenous, intramuscular, subcutaneous or oral dosage range from 50 ug daily to 100 mg daily;

choline chloride, dosage range from 500 mg daily to 30 grams daily;

choline bitartrate, dosage range from 500 mg daily to 30 grams daily;

bifemelane, dosage range from 1 mg/kg daily to 1.2 grams/kg daily;

vesamicol, dosage range from 50 ug/kg daily to 500 mg/kg daily;

secoverine, dosage range from 50 ug/kg daily to 500 mg/kg daily;

tetraphenylurea, dosage range from 50 ug/kg daily to 500 mg/kg daily; and nicotinamide, dosage range from 1 mg/kg daily to 500 mg/kg daily;

(l) postsynaptic receptor agonists such as arecoline, intravenous, intramuscular, subcutaneous or oral dosage range from 2 mg daily to 25 mg daily;

oxotremorine, intravenous, intramuscular, subcutaneous or oral dosage range from 1 ug/kg daily to 0.2 mg/kg daily;

ethyl nipecotate, intravenous, intramuscular, subcutaneous or oral dosage range from 2 mg daily to 250 mg daily;

bethanechol (Urecholine, Merck & Co.), dosage range from 5 mg daily to 200 mg daily; and levacecarnine (acetyl-L-carnitine or Alcar, Sigma-Tau), dosage range from 500 mg daily to 5 grams daily;

(m) ganglioside $GM_1$, intravenous, intramuscular or subcutaneous dosage range from 20 mg daily to 200 mg daily;

(n) specific monoamine oxidase-A inhibitors such as moclobemide (Aurorix, Hoffmann-La Roche), dosage range from 50 mg daily to 600 mg daily;

(o) N-methyl-D-aspartate glutamate receptor antagonists administered orally, intravenously, intramuscularly or subcutaneously such as milacemide, dosage range from 50 mg daily to 2.5 grams daily;

trihexyphenidyl (Artane, Lederle), dosage range from 0.1 mg daily to 20 mg daily;

ethopropazine (Paridol), dosage range from 10 mg daily to 400 mg daily;

procyclidine (Kemadrin, Burroughs Wellcome), dosage range from 1 mg daily to 40 mg daily;

diphenhydramine (Benadryl, Parke-Davis), dosage range from 5 mg daily to 200 mg daily;

dizocilpine (NeuroQard, Merck Sharp & Dohme), dosage range from 0.1 ug/kg daily to 10 mg/kg daily;

amantadine (Symmetrel, Du Pont Multi-Source Products), dosage range from 10 mg daily to 400 mg daily; and memantine, dosage range from 10 mg daily to 400 mg daily;

(p) nonsteroidal anti-inflammatory agents such as those recognized for treatment of rheumatoid arthritis, including flurbiprofen (Ansaid, Upjohn), dosage range from 20 mg daily to 300 mg daily;

aspirin (Arthritis Pain Formula, Whitehall Laboratories), dosage range from 250 mg aspirin daily to 4 gm daily, with the proviso that if the practice of this invention includes the use of aspirin in combination with PABA or the potassium or sodium salts of PABA, than at least one other co-agent is also included;

mesalamine (Asacol, Procter & Gamble Pharmaceuticals), dosage range from 250 mg daily to 2.4 gm daily;

phenylbutazone (Butazolidin, Geigy), dosage range from 30 mg daily to 400 mg daily;

sulindac (Clinoril, Merck & Co), dosage range from 40 mg daily to 400 mg daily;

penicillamine (Cuprimine, Merck & Co.), dosage range from 25 mg daily to 2 gm daily;

oxaprozin (Daypro, Searle), dosage range from 25 mg daily to 2 gm daily;

salsalate (Disalcid, 3M Pharmaceuticals), dosage range from 300 mg daily to 3 gm daily;

diflunisal (Dolobid, Merck & Co.), dosage range from 100 mg daily to 1.5 gm daily;

piroxicam (Feldene, Pfizer Labs Division), dosage range from 2 mg daily to 20 mg daily;

indomethacin (Indocin, Merck & Co.), dosage range from 10 mg daily to 200 mg daily;

etodolac (Lodine, Wyeth-Ayerst Laboratories), dosage range from 100 mg daily to 1.2 gm daily;

meclofenamate sodium (Meclomen, Parke-Davis), dosage range from 20 mg daily to 400 mg daily;

ibuprofen (Motrin, Upjohn), dosage range from 100 mg daily to 3.2 gm daily;

fenoprofen calcium (Nalfon, Dista), dosage range from 100 mg daily to 3.2 gm;

naproxen sodium (Anaprox, Syntex), dosage range from 50 mg daily to 1.65 gm daily;

naproxen (Naprosyn, Syntex), dosage range from 50 mg daily to 1.5 gm daily;

ketoprofen (Orudis, Wyeth-Ayerst), dosage range from 15 mg daily to 300 mg daily;

mefenamic acid (Ponstel, Parke-Davis), dosage range from 150 mg daily to 1.5 gm daily;

nabumetone (Relafen, SmithKline Beecham), dosage range from 100 mg daily to 2 gm daily;

auranofin (Ridaura, SmithKline Beecham), dosage range from 1 mg daily to 9 mg daily;

tolmetin sodium (Tolectin, McNeil Pharmaceutical), dosage range from 100 mg daily to 1.8 gm daily;

ketorolac tromethamine (Toradol, Syntex Laboratories), dosage range from 4 mg daily to 40 mg daily;

diclofenac sodium (Voltaren, Geigy), dosage range from 10 mg daily to 200 mg daily; and deferoxamine mesylate (Desferal, CIBA Pharmaceutical), intravenous, intramuscular or subcutaneous dosage range from 100 mg daily to 2 gm daily;

(r) selegiline (Eldepryl, Somerset), dosage range from 5 mg daily to 10 mg daily;

(s) thiamine, dosage range from 500 mg daily to 3 gm daily;

(t) anfacine, intravenous, intramuscular, subcutaneous or oral dosage range from 1 mg/kg daily to 350 mg/kg daily;

(u) sulbutiamine (Arcalion, Laboratories Servier), dosage range from 1 mg/kg daily to 350 mg/kg daily;

(v) antioxidant agents which may be used in combination such as ascorbic acid, dosage range from 1 mg daily to 60 mg daily;

N-acetylcysteine, dosage range from 100 mg daily to 1 gm daily;

penicillamine, dosage range from 25 mg daily to 2 gm daily;

cysteamine, dosage range from 200 mg daily to 4 gm daily; and deferoxamine mesylate (Desferal, CIBA Pharmaceutical), intravenous, intramuscular or subcutaneous dosage range from 100 mg daily to 2 gm daily;

(w) specific monoamine oxidase-B inhibitors such as lazabemide (Hoffmann-La Roche), dosage range from 10 mg daily to 200 mg daily;

(x) linopirdine (Aviva, DuPont Merck), dosage range from 1 mg daily to 500 mg daily;

(y) D-cycloserine, dosage range from 0.1 mg/kg daily to 15 mg/kg daily; and (z) serotonergic receptor antagonists such as ketanserin (Ketan, Janssen Pharmaceutica), intravenous, intramuscular, subcutaneous or oral dosage range from 0.1 mg/kg daily to 20 mg/kg daily; and mianserin (Mian, Organon International), intravenous, intramuscular, subcutaneous or oral dosage range from 0.1 mg/kg daily to 20 mg/kg daily.

EXAMPLE 3

Clinical treatment of various forms of diabetes can be improved by use of at least one primary agent of the present invention as disclosed in section (3), optionally in combination with one or more substances selected from sections (5) through (10), inclusive, and optionally in combination with one or more co-agent medicament to treat the disease or a symptom thereof, said medicament including co-agent use of:

(a) various insulin derivatives and compositions such as human isophane insulin suspension (Mixtard Human 70/30, Novo Nordisk), available in 100 unit/ml vials, dosage as per the Physician's Desk Reference [Dowd, AL, 1993, pg. 1684]);

human zinc suspension insulin (Novolin L, Novo Nordisk), available in 100 unit/ml vials, dosage as per the *Physician's Desk Reference* [Dowd, AL, 1993, pgs. 1683–1684]); and human insulin (HUMULIN compositions, Eli Lilly, available in seven formulations for intravenous use, dosage as per the *Physician's Desk Reference* [Dowd, AL, 1993, pgs. 1301–1308]);

(b) various oral sulfanilamide derivative hypoglycemic agents such as tolbutamide (Orinase, Upjohn), dosage range from 100 mg daily to 3 gm daily;

acetohexamide, dosage range from 25 mg daily to 1.5 gm daily; tolazamide (Tolinase, Upjohn), dosage range from 10 mg daily to 1 gm daily;

chlorpropamide (Diabinase, Pfizer Labs Division), dosage range from 10 mg daily to 500 mg daily;

glipizide (Glucotrol, Pratt Pharmaceuticals), dosage range from 1 mg daily to 40 mg daily; and glyburide (Micronase, Upjohn), dosage range from 0.5 mg daily to 20 mg daily;

(c) angiotensin-converting enzyme inhibitors such as captopril (Canoten, Squibb), dosage range from 10 mg daily to 450 mg daily;

captopril in combination with hydrochlorothiazide (Capozide, Squibb), dosage range from 6.25 mg captopril and 3.75 mg hydrochlorothiazide daily to 150 mg captopril and 50 mg hydrochlorothiazide daily;

enalapril maleate (Vasotec, Merck & Co.), dosage range from 1 mg daily to 40 mg daily;

enalapril maleate/hydrochlorothiazide combination (Vaseretic, Merck & Co.), dosage range from 2.5 mg enalapril and 6.25 mg hydrochlorothiazide daily to 20 mg enalapril and 50 mg hydrochlorothiazide daily;

epi-captopril, dosage range from 1 mg daily to 300 mg daily; and zofenoprilat, dosage range from 1 mg daily to 150 mg daily;

(d) anti-hyperlipidemia agents such as fibric acid derivatives including gemfibrozil (Lopid, Parke-Davis), dosage range from 100 mg daily to 1.2 gm daily;

clofibrate (Atromid-S, Wyeth-Ayerst), dosage range from 20 mg daily to 2 gm daily;

bezafibrate, dosage range from 100 mg daily to 1.3 grams daily;

fenofibrate, dosage range from 40 mg daily to 500 mg daily;

metformin, dosage range from 100 mg daily to 4 grams daily;

guar gum, dosage range from 2 grams daily to 20 grams daily;

3-hydroxy-3-methyl-glutaryl-CoA reductase inhibitors such as lovastatin (Mevacor, Merck & Co.), dosage range from 2 mg daily to 80 mg daily;

pravastatin sodium (Pravachol, Squibb), dosage range from 1 mg daily to 40 mg daily; and simvastatin (Zocor, Merck & Co.), dosage range from 1 mg daily to 40 mg daily;

dextrothyroxine sodium (Choloxin, Boots-Flint), dosage range from 0.25 mg daily to 8 mg daily;

probucol (Lorelco, Marion Merrell Dow), dosage range from 100 mg daily to 1 gm daily;

nicotinic acid (Nicolar, Rhone-Poulenc Rorer), dosage range from 500 mg daily to 6 gm daily;

acipimox, dosage range from 1 mg/kg daily to 500 mg/kg daily; or bile acid sequestrants such as cholestyramine resin (Ouestran Light, Bristol Laboratories), dosage range from 400 mg anhydrous cholestyramine resin daily to 20 gm anhydrous cholestyramine resin daily; and colestipol (Colestid, Upjohn), dosage range from 500 mg daily to 30 gm daily;

(e) antioxidants such as combinations consisting of ascorbic acid (dosage range from 1 mg daily to 60 mg daily), α-tocopherol (dosage range from 200 I. U. daily to 3,500 I. U. daily), β-carotene (1 mg daily to 100 mg daily) and the antioxidant co-agent selenium (dosage range from 25 ug daily to 0.5 mg daily);

(f) immunosuppressive drugs such as cyclosporine (Sandimmune, Sandoz Pharmaceutical), dosage range from 1 mg/kg daily to 15 mg/kg daily;

azathioprine (Imuran, Burroughs Wellcome), dosage range from 0.25 mg/kg daily to 5 mg/kg daily; and azathioprine/glucocorticoid combinations such as azathioprine in a dosage range from 0.25 mg/kg daily to 5 mg/kg daily in combination with intravenous, intramuscular, subcutaneous or oral methyl prednisolone, dosage range from 0.1 mg/kg daily (or alternate day) to 5 mg/kg daily (or alternate day);

(g) agents which decrease blood platelet aggregation such as acetylsalicylic acid (Ecotrin, SmithKline Beecham Consumer Brands), dosage range from 25 mg daily to 4 gm daily; and dipyridamole (Persantine, Boehringer Ingelheim), dosage range from 25 mg daily to 400 mg daily;

(h) agents which decrease blood viscosity such as pentoxifylline (Trental, Hoechst-Roussel), dosage range from 100 mg daily to 1.2 gm daily;

(i) analgesic agents for treatment of chronic pain such as acetaminophen (Extra Strength Tylenol, McNeil Consumer), dosage range from 300 mg daily to 4 gm daily;

(j) various agents for treatment of diabetes-related nephrotic syndrome such as furosemide (Lasix, Hoechst-Roussel), dosage range from 5 mg daily to 600 mg daily;

metolazone (Mykrox, Fisions Pharmaceuticals), dosage range from 0.1 mg daily to 1 mg daily;

lovastatin (Mevacor, Merck & Co.), dosage range from 2 mg daily to 80 mg daily;

heparin sodium (Tubex, Wyeth-Ayerst), intravenous, intramuscular or subcutaneous dosage range from 1,000 USP units daily to 20,000 USP units daily;

warfarin sodium (Coumadin, Du Pont Pharmaceutical), dosage range from 0.25 mg daily to 10 mg daily; and aminoguanidine (Alteon), intravenous, intramuscular, subcutaneous or oral dosage range from 5 mg/kg daily to 100 mg/kg daily; and (k) aldose reductase inhibitors such as sorbinil (Pfizer), intravenous, intramuscular, subcutaneous or oral dosage range from 1 mg/kg daily to 25 mg/kg daily;

(E)-3-carboxymethyl-5-[(2E)-methyl-3-phenylpropenylidene]rhodanine, intravenous, intramuscular, subcutaneous or oral dosage range from 1 mg/kg daily to 40 mg/kg daily;

alrestatin, intravenous, intramuscular, subcutaneous or oral dosage range from 1 mg/kg daily to 100 mg/kg daily;

statil, intravenous, intramuscular, subcutaneous or oral dosage range from 1 mg/kg daily to 25 mg/kg daily; and tolrestat (Ayerst-Wyeth Laboratories), intravenous, intramuscular, subcutaneous or oral dosage range from 1 mg/kg daily to 25 mg/kg daily.

EXAMPLE 4

Clinical treatment of symptomology related to aging can be improved by use of at least one primary agent of the present invention as disclosed in section (3), optionally in combination with one or more substances selected from sections (5) through (10), inclusive, and optionally in combination with one or more co-agent medicament to treat the aging process or a symptom thereof, said medicament including co-agent use of:

(a) monoamine oxidase B inhibitors such as selegiline (Eldepryl, Somerset), dosage range from 5 mg daily to 10 mg daily;

(b) acetylcholinesterase inhibitors such as physostigmine (Antilirium Injectable, Forest Pharmaceuticals), oral dosage range from 0.1 mg daily to 20 mg daily, or intravenous, intramuscular or subcutaneous dosage range from 5 ug daily to 3 mg daily, optionally with phosphatidylcholine co-agent, oral dosage range from zero to 15 gm daily;

heptylphysostigmine, dosage range from 1 mg daily to 1 gram daily; tacrine (Cognex, Warner-Lambert), dosage range from 5 mg daily to 200 mg daily, optionally with phosphatidylcholine co-agent, dosage range from zero to 15 gm daily;

(+/−)-9-amino-1,2,3,4-tetrahydroacridin-1-ol, dosage range from 2 mg daily to 200 mg daily;

metrifonate, intramuscular, intravenous, subcutaneous or oral dosage range from 0.1 mg/kg daily to 125 mg/kg daily;

velnacrine maleate (Mentane, Hoechst-Roussel), dosage range from 10 mg daily to 350 mg daily;

methanesulfonyl fluoride, intravenous, intramuscular, subcutaneous or oral dosage range from 5 mg/kg daily to 350 mg/kg daily;

phenylmethylsulfonyl fluoride, intravenous, subcutaneous, intramuscular or oral dosage range from 5 mg/kg daily to 60 mg/kg daily;

huperzine A, intramuscular, intravenous, subcutaneous or oral dosage range from 10 ug/kg daily to 1 mg/kg daily;

huperzine B, intramuscular, intravenous, subcutaneous or oral dosage range from 10 ug/kg daily to 1 mg/kg daily;

edrophonium chloride (Hoffman LaRoche), intravenous, intramuscular, subcutaneous or oral dosage range from 2 mg daily to 400 mg daily;

galanthamine, intravenous, intramuscular, subcutaneous or oral dosage range from 5 mg daily to 100 mg daily; and miotine, intravenous, intramuscular, subcutaneous or oral dosage range from 2 mg daily to 400 mg daily;

(c) angiotensin-converting enzyme inhibitors such as captopril (Capoten, Squibb), dosage range from 5 mg daily to 300 mg daily;

captopril in combination with hydrochlorothiazide (Capozide, Squibb), dosage range from 5 mg captopril and 3 mg hydrochlorothiazide daily to 150 mg captopril and 50 mg hydrochlorothiazide daily;

enalapril maleate (Vasotec, Merck & Co.), dosage range from 0.5 mg daily to 100 mg daily;

enalaprilat, dosage range from 0.5 mg daily to 100 mg daily;

enalapril maleate/hydrochlorothiazide combination (Vaseretic, Merck & Co.), dosage range from 2.5 mg enalapril maleate and 6.25 mg hydrochlorothiazide daily to 20 mg enalapril maleate and 50 mg hydrochlorothiazide daily;

fosinopril (Monopril, Mead Johnson Pharmaceuticals), dosage range from 2 mg daily to 60 mg daily;

lisinopril (Zestril, Stuart), dosage range from 1 mg daily to 40 mg daily;

ramipril (Altace, Hoechst-Roussel), dosage range from 0.5 mg daily to 10 mg daily;

epi-captopril, dosage range from 1 mg daily to 300 mg daily;

alacepril, dosage range from 5 mg daily to 300 mg daily;

quinapril, dosage range from 0.5 mg daily to 40 mg daily;

perindopril, dosage range from 0.2 mg daily to 40 mg daily;

delapril, dosage range from 4 mg daily to 1.5 grams daily;

cilazapril, dosage range from 0.2 mg daily to 40 mg daily;

pivalopril, dosage range from 2 mg daily to 250 mg daily;

rentiapril, dosage range from 1 mg daily to 150 mg daily;

zofenopril, dosage range from 1 mg daily to 150 mg daily; and zofenoprilat, dosage range from 1 mg daily to 150 mg daily;

(d) N-methyl-D-aspartate glutamate receptor antagonists administered orally, subcutaneously, intramuscularly or intravenously such as milacemide, dosage range from 50 mg daily to 2.5 grams daily;

trihexyphenidyl (Artane, Lederle), dosage range from 0.1 mg daily to 20 mg daily;

ethopropazine (Paridol), dosage range from 10 mg daily to 400 mg daily;

procyclidine (Kemadrin, Burroughs Wellcome), dosage range from 1 mg daily to 40 mg daily;

diphenhydramine (Benadryl, Parke-Davis), dosage range from 5 mg daily to 200 mg daily;

dizocilpine (Neurogard, Merck Sharp & Dohme), dosage range from 0.1 ug/kg daily to 10 mg/kg daily;

amantadine (Symmetrel, Du Pont Multi-Source Products), dosage range from 10 mg daily to 400 mg daily; and memantine, dosage range from 10 mg daily to 400 mg daily;

(e) the antioxidant co-agent ascorbic acid, dosage range from 1 mg daily to 60 mg daily;

(f) vasodilator and other nootropic direct brain metabolic enhancer drugs such as flunarizine, dosage range from 2 mg daily to 100 mg daily;

nimodipine (Nimotop, Miles Pharmaceutical), dosage range from 300 mg daily to 3.6 gm daily;

idebenone, dosage range from 5 mg/kg daily to 150 mg/kg daily;

ebiratide, subcutaneous dosage range from 3 ug/kg daily to 1 mg/kg daily;

vinpocetine (Cavinton, Chemical Works of Gedeon Richter, Ltd.), intravenous or oral dosage range from 5 mg/kg daily to 300 mg/kg daily;

pentoxifylline, dosage range from 50 mg daily to 3 grams daily;

citicoline, dosage range from 50 mg daily to 5 grams daily;

bromvincamine, dosage range from 25 mg daily to 3 grams daily;

cyclandelate, dosage range from 25 mg daily to 3 grams daily;

isoxsuprene, dosage range from 25 mg daily to 3 grams daily;

nafronyl, dosage range from 25 mg daily to 3 grams daily;

papaverine, dosage range from 25 mg daily to 3 grams daily;

suloctidil, dosage range from 25 mg daily to 3 grams daily;

vinburnine, dosage range from 25 mg daily to 3 grams daily;

vincamine, dosage range from 25 mg daily to 3 grams daily;

vindeburnol, dosage range from 25 mg daily to 3 grams daily;

nicergoline (Sermion), intravenous, intramuscular, subcutaneous or oral dosage range from 6 mg daily to 10 grams;

razobazam, intravenous, intramuscular, subcutaneous or oral dosage range from 0.1 mg/kg daily to 25 mg/kg daily;

exifone, intravenous, intramuscular, subcutaneous or oral dosage range from 1 mg daily to 1 gram daily;

rolipram, intravenous, intramuscular, subcutaneous or oral dosage range from 1 mg daily to 1 gram daily;

naloxone, intravenous, intramuscular, subcutaneous or oral dosage range from 5 mg daily to 200 mg daily;

ethyl 5-isopropyloxy-4-methyl-$\beta$-carboline-3-carboxylate, intravenous, intramuscular, subcutaneous or oral dosage range from 2 mg/kg daily to 100 mg/kg daily;

N'-methyl-$\beta$-carboline-3-carboxamide, intravenous, intramuscular, subcutaneous or oral dosage range from 2 mg/kg daily to 100 mg/kg daily;

methyl 6,7-dimethoxy-4-ethyl-$\beta$-carboline-3-carboxylate, intravenous, intramuscular, subcutaneous or oral dosage range from 0.1 mg/kg daily to 10 mg/kg daily;

ethyl 5-methoxy-4-ethyl-$\beta$-carboline-3-carboxylate, intravenous, intramuscular, subcutaneous or oral dosage range from 1 mg/kg daily to 30 mg/kg daily;

sabeluzole, dosage range from 2 mg daily to 40 mg daily;
phosphatidylserine, intravenous, intramuscular, subcutaneous or oral dosage range from 1 mg/kg daily to 250 mg/kg daily;
piracetam, dosage range from 50 mg/kg daily to 8 grams/kg daily;
aniracetam, dosage range from 50 mg/kg daily to 1 gram/kg daily;
pyroglutamic acid, intravenous, intramuscular, subcutaneous or oral dosage range from 100 mg/kg daily to 5 grams/kg daily;
tenilsetam, dosage range from 10 mg daily (or alternate day) to 1 gram daily (or alternate day), or from 25 mg once a week to 1 gram once a week;
pramiracetam, dosage range from 50 mg/kg daily to 8 grams/kg daily;
oxiracetam, dosage range from 200 mg daily to 2 grams daily;
rolziracetam, intravenous, intramuscular, subcutaneous or oral dosage range from 1 mg daily to 1 gram daily;
etiracetam, dosage range from 50 mg/kg daily to 8 grams/kg daily;
propentophylline, intravenous, intramuscular, subcutaneous or oral dosage range from 50 mg daily to 3 grams daily;
dupracetam, intravenous, intramuscular, subcutaneous or oral dosage range from 1 mg daily to 1 gram daily; and
ergoloid mesylates (Hydergine, Sandoz Pharmaceuticals), dosage range from 0.5 mg daily to 40 mg daily;
(g) postsynaptic receptor agonists such as
arecoline, subcutaneous or oral dosage range from 2 mg daily to 25 mg daily;
oxotremorine, intravenous, intramuscular, subcutaneous or oral dosage range from 1 ug/kg daily to 0.2 mg/kg daily; and
bethanechol (Urecholine, Merck & Co.), dosage range from 5 mg daily to 200 mg daily;
levacecarnine (acetyl-L-carnitine or Alcar, Sigma-Tau), dosage range from 500 mg daily to 5 grams daily; and
ethyl nipecotate, intravenous, intramuscular, subcutaneous or oral dosage range from 2 mg daily to 250 mg daily;
(h) biogenic amines and co-agents related thereto such as
clonidine (Catapres, Boehringer Ingelheim), dosage range from 20 ug daily to 2.4 mg daily;
guanfacine (Tenex, Robins), dosage range from 0.25 mg daily to 3 mg daily;
alaproclate, dosage range from 0.25 mg daily to 3 mg daily;
fipexide, dosage range from 0.25 mg daily to 3 mg daily;
zimeldine, dosage range from 0.25 mg daily to 3 mg daily; and
citalopram, dosage range from 0.25 mg daily to 3 mg daily;
(i) anfacine, intravenous, intramuscular, subcutaneous or oral dosage range from 1 mg/kg daily to 350 mg/kg daily;
(j) agents which may enhance acetylcholine synthesis, storage or release such as
phosphatidylcholine, dosage range from 1 gm daily to 15 gm daily;
4-aminopyridine, intravenous, intramuscular, subcutaneous or oral dosage range from 0.25 mg/kg daily to 10 mg/kg daily;
3,4-diaminopyridine, intravenous, intramuscular, subcutaneous or oral dosage range from 50 ug daily to 100 mg daily;
choline chloride, dosage range from 500 mg daily to 30 grams daily;
choline bitartrate, dosage range from 500 mg daily to 30 grams daily;
bifemelane, dosage range from 1 mg/kg daily to 1.2 grams/kg daily;
vesamicol, dosage range from 50 ug/kg daily to 500 mg/kg daily;
secoverine, dosage range from 50 ug/kg daily to 500 mg/kg daily;
tetraphenylurea, dosage range from 50 ug/kg daily to 500 mg/kg daily; and
nicotinamide, dosage range from 1 mg/kg daily to 500 mg/kg daily;
(k) acetylhomocysteine thiolactone, intravenous, intramuscular, subcutaneous or oral dosage range from 0.5 mg/kg daily to 25 mg/kg daily;
(l) ganglioside $GM_1$, intravenous, intramuscular or subcutaneous dosage range from 20 mg daily to 200 mg daily;
(m) sulbutiamine, dosage range from 1 mg/kg daily to 350 mg/kg daily; and
(n) serotonergic receptor antagonists such as
ketanserin (Ketan, Janssen Pharmaceutica), intravenous, intramuscular, subcutaneous or oral dosage range from 0.1 mg/kg daily to 20 mg/kg daily; and
mianserin (Mian, Organon International), intravenous, intramuscular, subcutaneous or oral dosage range from 0.1 mg/kg daily to 20 mg/kg daily.

EXAMPLE 5

Clinical treatment of tinnitus (nerve deafness) can be improved by use of at least one primary agent of the present invention as disclosed in section (3), optionally in combination with one or more substances selected from sections (5) through (10), inclusive, and optionally in combination with one or more co-agent medicament to treat the disease or a symptom thereof, said medicament including co-agent use of:

(a) antidepressants or antianxiety medications such as
amitriptyline (Elavil, Stuart), dosage range from 50 mg daily to 300 mg daily;
amitriptyline/perphenazine combinations (Etrafon, Schering), dosage range from 4 mg perphenazine and 50 mg amitriptyline daily to 16 mg perphenazine and 100 mg amitriptyline daily;
alprazolam (Xanax, Upjohn), dosage range from 125 ug daily to 4 mg daily; and
triptolene, dosage range from 0.1 mg daily to 20 mg daily;
(b) anticonvulsants such as
primidone (Mysoline, Wyeth-Ayerst), dosage range from 10 mg daily to 2 gm daily;
phenytoin (Dilantin, Parke-Davis), dosage range from 10 mg daily to 600 mg daily; and
carbamazepine (TegQretol, Basel), dosage range from 40 mg daily to 1.6 gm daily;
(c) lidocaine (Xylocaine, Astra), intravenous, intramuscular or subcutaneous dosage range from 1 mg daily to 300 mg daily, or oral forms of lidocaine in a dosage range of 1 mg daily to 300 mg daily;
(d) tocainide, dosage range from 10 mg daily to 400 mg daily;

(e) flecinide, dosage range from 10 mg daily to 400 mg daily;

(f) nicotinamide, dosage range from 1 mg/kg daily to 500 mg/kg daily;

(g) aminooxyacetic acid, dosage range from 10 mg daily to 500 mg daily;

(h) praxilene, dosage range from 5 mg/kg daily to 100 mg/kg daily;

(i) aniracetam, dosage range from 50 mg/kg daily to 1 gram/kg daily;

(j) piracetam, dosage range from 1 mg daily to 100 mg daily;

(k) 13-cis-retinoic acid, dermal, subcutaneous, intravenous, intramuscular or oral dosage range from 50 ug/kg daily to 25 mg/kg daily; and (l) 13-trans-retinoic acid, dermal, subcutaneous, intravenous, intramuscular or oral dosage range from 50 ug/kg daily to 25 mg/kg daily.

EXAMPLE 6

Clinical treatment of multiple sclerosis may be improved by use of at least one primary agent of the present invention as disclosed in section (3), optionally in combination with one or more substances selected from sections (5) through (10), inclusive, and optionally in combination with one or more co-agent medicament to treat the disease or a symptom thereof, said medicament including co-agent use of:

(a) azathioprine (Imuran, Burroughs Wellcome), dosage range from 5 mg daily to 300 mg daily;

(b) copolymer-1 (random polymer of L-alanine, L-glutamic acid, L-lysine and L-tyrosine, ratio of 6.0:1.9:4.7:1.0, of molecular weight between 14,000 and 23,000 Daltons), intravenous, subcutaneous or intramuscular dosage range 2 mg daily to 40 mg daily;

(c) cyclosporine (Sandimmune, Sandoz Pharmaceutical), dosage range from 1 mg/kg daily to 15 mg/kg daily;

(d) interferons such as alfa-2a interferon (Roferon-A, Roche Laboratories), intravenous, intramuscular or subcutaneous dosage range from 300,000 IU daily to 36,000,000 IU daily;

alfa-2b interferon (Intron-A, Schering), intravenous, intramuscular or subcutaneous dosage range from 300,000 IU daily to 5,000,000 IU daily;

alfa-N3 interferon (Alferon N Injection, Purdue Frederick), intravenous, intramuscular or subcutaneous dosage range from 250,000 IU daily to 2,500,000 IU daily;

beta interferon (Betaseron, Berlex), intravenous, intramuscular or subcutaneous dosage range from 5,000 U/kg daily to 50,000 U/kg daily; and gamma-1b interferon (Actimmune, Genentech), intravenous, intramuscular or subcutaneous dosage range from 5,000 U/kg daily to 50,000 U/kg daily;

(e) corticosteroids such as prednisone (Deltasone, Upjohn), dosage range from 0.5 mg daily or every other day to 200 mg daily or every other day; and dexamethasone (Decadron, Merck & Co.), dosage range from 0.1 mg daily or every other day to 10 mg daily or every other day;

(f) cyclophosphamide (Cytoxan, Bristol-Myers Oncology), intravenous, intramuscular, subcutaneous or oral dosage range from 0.1 mg/kg daily to 10 mg/kg daily;

(g) 4-aminopyridine, intravenous, intramuscular, subcutaneous or oral dosage range from 0.25 mg/kg daily to 10 mg/kg daily;

(h) baclofen (Atrofen, Athena Neurosciences), dosage range from 1 mg daily to 80 mg daily; and (i) 3,4-diaminopyridine, dosage range from 50 ug daily to 100 mg daily.

EXAMPLE 7

Clinical treatment of amyotrophic lateral sclerosis can be improved by use of at least one primary agent of the present invention as disclosed in section (3), optionally in combination with one or more substances selected from sections (5) through (10), inclusive, and optionally in combination with one or more co-agent medicament to treat the disease or a symptom thereof, said medicament including co-agent use of:

(a) thyrotropin releasing factor (Relefact TRH, Ferring); intraveneous, subcutaneous or intramuscular dosage range from 0.5 mg daily to 500 mg daily;

(b) serine, dosage range from 500 mg daily to 15 gm daily;

(c) L-threonine, dosage range from 500 mg daily to 15 gm daily;

(d) N-methyl-D-aspartate glutamate receptor antagonists administered orally, intramuscularly, subcutaneously or intravenously such as milacemide, dosage range from 50 mg daily to 2.5 grams daily;

trihexyphenidyl (Artane, Lederle), dosage range from 0.1 mg daily to 20 mg daily;

ethopropazine (Paridol), dosage range from 10 mg daily to 400 mg daily;

procyclidine (Kemadrin, Burroughs Wellcome), dosage range from 1 mg daily to 40 mg daily;

diphenhydramine (Benadryl, Parke-Davis), dosage range from 5 mg daily to 200 mg daily;

dizocilpine (Neurogard, Merck Sharp & Dohme), dosage range from 0.1 ug/kg daily to 10 mg/kg daily;

amantadine (Symmetrel, Du Pont Multi-Source Products), dosage range from 10 mg daily to 400 mg daily; and memantine, dosage range from 10 mg daily to 400 mg daily.

EXAMPLE 8

Clinical treatment of Huntington's disease can be improved by use of at least one primary agent of the present invention as disclosed in section (3), optionally in combination with one or more substances selected from sections (5) through (10), inclusive, and optionally in combination with one or more co-agent medicament to treat the disease or a symptom thereof, said medicament including co-agent use of:

(a) N-methyl-D-aspartate glutamate receptor antagonists administered orally, intramuscularly, subcutaneously or intravenously such as milacemide, dosage range from 50 mg daily to 2.5 grams daily;

trihexyphenidyl (Artane, Lederle), dosage range from 0.1 mg daily to 20 mg daily;

ethopropazine (Paridol), dosage range from 10 mg daily to 400 mg daily;

procyclidine (Kemadrin, Burroughs Wellcome), dosage range from 1 mg daily to 40 mg daily;

diphenhydramine (Benadryl, Parke-Davis), dosage range from 5 mg daily to 200 mg daily;

dizocilpine (Neurogard, Merck Sharp & Dohme), dosage range from 0.1 ug/kg daily to 10 mg/kg daily;

amantadine (Symmetrel, Du Pont Multi-Source Products), dosage range from 10 mg daily to 400 mg daily; and memantine, dosage range from 10 mg daily to 400 mg daily;

(b) agents which may enhance acetylcholine synthesis, storage or release such as phosphatidylcholine, dosage range from 1 gm daily to 15 gm daily;

3,4-diaminopyridine, dosage range from 50 ug daily to 100 mg daily;

choline chloride, dosage range from 500 mg daily to 20 grams daily;

and choline bitartrate, dosage range from 500 mg daily to 20 grams daily; and (c) postsynaptic receptor agonists such as arecoline, intravenous, intramuscular, subcutaneous or oral dosage range from 2 mg daily to 25 mg daily.

EXAMPLE 9

Clinical treatment of olivopontocerebellar atrophy can be improved by use of at least one primary agent of the present invention as disclosed in section (3), optionally in combination with one or more substances selected from sections (5) through (10), inclusive, and optionally in combination with one or more co-agent medicament to treat the disease or a symptom thereof, said medicament including co-agent use of:

N-methyl-D-aspartate glutamate receptor antagonists administered orally, subcutaneously, intramuscularly or intravenously such as milacemide, dosage range from 50 mg daily to 2.5 grams daily;

trihexyphenidyl (Artane, Lederle), dosage range from 0.1 mg daily to 20 mg daily;

ethopropazine (Paridol), dosage range from 10 mg daily to 400 mg daily;

procyclidine (Kemadrin, Burroughs Wellcome), dosage range from 1 mg daily to 40 mg daily;

diphenhydramine (Benadryl, Parke-Davis), dosage range from 5 mg daily to 200 mg daily;

dizocilpine (Neurogard, Merck Sharp & Dohme), dosage range from 0.1 ug/kg daily to 10 mg/kg daily;

amantadine (Symmetrel, Du Pont Multi-Source Products), dosage range from 10 mg daily to 400 mg daily; and memantine, dosage range from 10 mg daily to 400 mg daily.

EXAMPLE 10

Clinical treatment of alcoholic polyneuropathy can be improved by use of at least one primary agent of the present invention as disclosed in section (3), optionally in combination with one or more substances selected from sections (5) through (10), inclusive, and optionally in combination with one or more co-agent medicament to treat the disease or a symptom thereof, said medicament including co-agent use of:

(a) tiapride, dosage range from 1 mg daily to 400 mg daily;

(b) physostigmine (Antilirium Injectable, Forest Pharmaceuticals), oral dosage range from 0.1 mg daily to 20 mg daily, or intravenous, intramuscular or subcutaneous dosage range from 5 ug daily to 3 mg daily, optionally with phosphatidylcholine co-agent, oral dosage range from zero to 15 gm daily;

(c) piracetam, dosage range from 1 mg daily to 100 mg daily; and (d) cyclandelate, dosage range from 25 mg daily to 3 grams daily.

EXAMPLE 11

Clinical treatment of hereditary motor and sensory neuropathies can be improved by use of at least one primary agent of the present invention as disclosed in section (3), optionally in combination with one or more substances selected from sections (5) through (10), inclusive, and optionally in combination with one or more co-agent medicament to treat the disease or a symptom thereof, said medicament including co-agent use of:

3,4-diaminopyridine, intravenous, intramuscular or subcutaneous dosage range from 50 ug daily to 100 mg daily.

EXAMPLE 12

Clinical treatment of urinary incontinence resulting from Alzheimer's senile dementia, demyelinating diseases such as multiple sclerosis, peripheral nerve lesions, diabetes mellitus and alcoholic polyneuropathy can be improved by use of at least one primary agent of the present invention as disclosed in section (3), optionally in combination with one or more substances selected from sections (5) through (10), inclusive, and optionally in combination with one or more co-agent medicament to treat the disease or a symptom thereof, said medicament including co-agent use of:

(a) cholinergics such as bethanechol (Urecholine, Merck & Co.), dosage range from 5 mg daily to 200 mg daily alone, or in combination with prazosin, dosage range from 0.5 mg daily to 4 mg daily;

(b) anti-cholinergics such as hyoscyamine sulfate, dosage range from 0.1 mg daily to 1 mg daily;

atropine sulfate, dosage range from 25 ug daily to 0.2 mg daily;

propantheline (Pro-Banthine, Schiapparelli Searle), dosage range from 2.5 mg daily to 75 mg daily;

oxybutynin (Ditropan, Marion Merrell Dow), dosage range from 2.5 mg daily to 20 mg daily; and dicyclomine (Bentyl, Marion Merrell Dow), dosage range from 10 mg daily to 160 mg daily;

(c) α-adrenergics such as ephedrine, dosage range from 10 mg daily to 150 mg daily; and phenylpropanolamine, dosage range from 10 mg daily to 150 mg daily;

(d) tricyclic agents such as imipramine (Tofranil, Geigy), dosage range from 10 mg daily to 200 mg daily; and doxepin (Adapin, Lotus Biochemical), dosage range from 10 mg daily to 300 mg daily;

(e) flavoxate (Uripas, SmithKline Beecham Pharmaceuticals), dosage range from 30 mg daily to 800 mg daily;

(f) β-adrenergic blockers such as propranolol (Inderal, Wyeth-Ayerst Laboratories), dosage range from 30 mg daily to 640 mg daily;

pindolol (Visken, Sandoz Pharmaceuticals), dosage range from 10 mg daily to 60 mg daily;

metoprolol tartrate (Lopressor, Geigy), dosage range from 100 mg daily to 450 mg daily;

metoprolol succinate (Toprol XL, Astra), dosage range from 50 mg daily to 400 mg daily; and atenolol (Tenormin, ICI Pharma), dosage range from 50 mg daily to 200 mg daily; and (g) vasopressin analogues such as desmopressin (DDAVP Nasal Spray, Rhone-Poulenc Rorer Pharmaceuticals), dosage range from 10 ug daily to 40 ug daily.

EXAMPLE 13

Clinical treatment of gastroesophageal reflux disease, hypoperistalsis and/or delayed gastric emptying can be improved by use of at least one primary agent of the present invention as disclosed in section (3), optionally in combination with one or more substances selected from sections (5) through (10), inclusive, and optionally in combination with one or more co-agent medicament to treat the disease or a symptom thereof, said medicament including co-agent use of:

(a) metoclopramide (Reglan, A. H. Robins), intravenous, intramuscular, subcutaneous or oral dosage range from 2 mg daily to 60 mg daily;

(b) cisapride (Prepulsid, Janssen Pharmaceutica), intravenous, intramuscular, subcutaneous or oral dosage range from 1 mg daily to 100 mg daily;

(c) famotidine (Pepcid, Merck & Co.), dosage range from 2 mg daily to 80 mg daily;

(d) cimetidine (Tagamet, SmithKline Beecham), dosage range from 40 mg daily to 1.6 gm daily;

(e) ranitidine (Zantac, Glaxo Pharmaceuticals), dosage range from 30 mg daily to 6 gm daily;

(f) omeprazole (Prilosec, Merck & Co.), dosage range from 5 mg daily to 400 mg daily; and (g) galanthamine, intravenous, intramuscular, subcutaneous or oral dosage range from 5 mg daily to 100 mg daily.

EXAMPLE 14

Clinical treatment of symptomology related to onset and development of atherosclerosis can be improved by use of at least one primary agent of the present invention as disclosed in section (3), optionally in combination with one or more substances selected from sections (5) through (10), inclusive, and optionally in combination with one or more co-agent medicament to treat the disease or a symptom thereof, said medicament including co-agent use of:

(a) angiotensin-converting enzyme inhibitor free radical scavenging agents possessing sulfhydryl groups such as captopril (Capoten, Squibb), dosage range from 5 mg daily to 300 mg daily;

captopril in combination with hydrochlorothiazide (Capozide, Squibb), dosage range from 5 mg captopril and 3 mg hydrochlorothiazide daily to 150 mg captopril and 50 mg hydrochlorothiazide daily;

epi-captopril, dosage range from 1 mg daily to 300 mg daily;

alacepril, dosage range from 5 mg daily to 300 mg daily;

pivalopril, dosage range from 2 mg daily to 250 mg daily; and rentiapril, dosage range from 1 mg daily to 150 mg daily;

(b) fibric acid derivative anti-hyperlipidemia agents such as gemfibrozil (Lopid, Parke-Davis), dosage range from 100 mg daily to 1.2 gm daily;

clofibrate (Atromid-S, Wyeth-Ayerst Laboratories), dosage range from 20 mg daily to 2 gm daily;

bezafibrate, dosage range from 100 mg daily to 1.3 grams daily; and fenofibrate, dosage range from 40 mg daily to 500 mg daily;

(c) metformin, dosage range from 100 mg daily to 4 grams daily;

(d) nicotinic acid (Nicolar, Rhone-Poulenc Rorer), dosage range from 500 mg daily to 6 gm daily;

(e) natural hydroscopic non-digestable edible plant carbohydrate polymers such as guar gum, dosage range from 2 grams daily to 20 grams daily;

(f) 3-hydroxy-3-methylglutaryl-CoA reductase inhibitors such as lovastatin (Mevacor, Merck & Co.), dosage range from 2 mg daily to 80 mg daily;

pravastatin (Pravachol, Squibb), dosage range from 1 mg daily to 40 mg daily; and simvastatin (Zocor, Merck & Co.), dosage range from 1 mg daily to 40 mg daily;

(g) acipimox, dosage range from 1 mg/kg daily to 500 mg/kg daily;

(h) bile acid sequestrants such as cholestyramine resin (Questran Light, Bristol Laboratories), dosage range from 400 mg anhydrous cholestyramine resin daily to 16 gm anhydrous cholestyramine resin daily; and colestipol (Colestid, Upjohn), dosage range from 500 mg daily to 30 gm daily;

(i) anti-hypertensive agents including oral diuretics such as bendroflumethiazide (Naturetin), dosage range from 0.5 mg daily to 5 mg daily;

benzthiazide (Exna), dosage range from 1 mg daily to 50 mg daily;

chlorothiazide (Diuril), dosage range from 10 mg daily to 500 mg daily;

chlorthalidone (Hvqroton), dosage range from 1 mg daily to 50 mg daily;

cyclothiazide (Anhydron), dosage range from 0.1 mg daily to 2 mg daily;

hydrochlorothiazide (Hydro-Diuril), dosage range from 1 mg daily to 50 mg daily;

hydroflumethiazide (Saluron), dosage range from 1 mg daily to 50 mg daily;

indapamide (Lozol), dosage range from 0.25 mg daily to 5 mg daily;

methylclothiazide (Enduron), dosage range from 0.25 mg daily to 5 mg daily;

metolazone (Zaroxolyn), dosage range from 0.1 mg daily to 10 mg daily;

polythiazide (Renese), dosage range from 0.2 mg daily to 4 mg daily;

quinethazone (Hydromox), dosage range from 2.5 mg daily to 100 mg daily;

trichlormethiazide (Nagua), dosage range from 0.1 mg daily to 4 mg daily; and idebenone, dosage range from 5 mg/kg daily to 150 mg/kg daily;

loop diuretics such as
bumetanide (Bumex), 50 ug daily to 10 mg daily;
ethacrynic acid (Edecrin), dosage range from 2.5 mg daily to 100 mg daily;
furosemide (Lasix), dosage range from 2 mg daily to 600 mg daily; and
torsemide (Presaril, Boehringer-Manheim), dosage range of 0.5 mg daily to 20 mg daily;
and potassium-sparing diuretics such as
   amiloride (Midamor), dosage range from 0.5 mg daily to 10 mg daily;
   spironolactone (Aldactone), dosage range from 2.5 mg daily to 400 mg daily; and
   triamterene (Dyrenium), dosage range from 5 mg daily to 150 mg daily;
β-adrenergic antagonists such as
   acebutolol (Sectral), dosage range from 20 mg daily to 1.2 gm daily;
   atenolol (Tenormin), dosage range from 2.5 mg daily to 200 mg daily;
   betaxolol (Kerlone), dosage range from 1 mg daily to 20 mg daily;
   carteolol (Cartrol), dosage range from 0.25 mg daily to 10 mg daily;
   labetalol (Normodyne), dosage range from 20 mg daily to 1.8 gm daily;
   metoprolol (Lopressor), 5 mg daily to 200 mg daily;
   nadolol (Corgard), dosage range from 4 mg daily to 240 mg daily;
   penbutolol (Levatol), dosage range from 2 mg daily to 80 mg daily;
   pindolol (Visken), dosage range from 0.5 mg daily to 60 mg daily;
   propranolol (Inderal or Inderal LA), dosage range from 4 mg daily to 320 mg daily;
   timolol (Blocadren), dosage range from 1 mg daily to 60 mg daily;
   and bisoprolol (Zebeta, Lederle), dosage range from 0.5 mg daily to 10 mg daily;
calcium antagonists such as
   diltiazem (Cardizem or Cardizem SR), dosage range from 10 mg daily to 360 mg daily;
   verapamil (Calan or Calan SR), dosage range from 10 mg daily to 480 mg daily;
   nifedipine (Procardia), dosage range from 3 mg daily to 180 mg daily;
   nifedipine (Procardia XL), dosage range from 3 mg daily to 90 mg daily;
   nicardipine (Cardene), dosage range from 6 mg daily to 120 mg daily;
   isradipine (DynaCirc), dosage range from 0.5 mg daily to 20 mg daily;
   amlodipine (Norvasc, Pfizer Labs Division), dosage range from 0.5 mg daily to 10 mg daily;
   felodipine (Plendil, Merck & Co.), dosage range from 0.5 mg daily to 20 mg daily;
   nimodipine (Nimotop, Miles Pharmaceutical), dosage range from 300 mg daily to 3.6 gm daily;
   flunarizine, dosage range from 2 mg daily to 100 mg daily;
angiotensin-converting enzyme inhibitors such as
   captopril (Capoten), dosage range from 2.5 mg daily to 300 mg daily;
   enalapril (Vasotec), dosage range from 0.25 mg daily to 40 mg daily;
   fosinopril (Monopril), dosage range from 1 mg daily to 60 mg daily;
   lisinopril (Zestril), dosage range from 0.5 mg daily to 40 mg daily;
   ramipril (Altace), dosage range from 0.25 mg daily to 10 mg daily;
   quinapril (Accupril, Parke-Davis), dosage range from 1 mg daily to 80 mg daily;
   quinapril/hydrochlorothiazide combinations (Accuretic, Parke-Davis), dosage range from 2 mg quinapril and 1.25 mg hydrochlorothiazide daily to 80 mg quinapril and 125 mg hydrochlorothiazide daily; and
   benazepril (Lotensin, CIBA Pharmaceutical), dosage range from 0.1 mg daily to 80 mg daily;
peptide-based renin inhibitors such as [(2S)-3-(4-methylpiperazin-11-yl)sulfonyl-2-(phenylmethyl)-propionyl]-N-[(1S,2R,3S)-1-(cyclohexylmethyl)-2,3-dihydroxy-5-methylhexyl]-L-[3-(thiazol-4-yl)alaninamide] (A-72517, Abbott Laboratories), oral, intravenous, intramuscular or subcutaneous dosage range from 0.1 mg/kg daily to 120 mg/kg daily;
centrally acting α-adrenergic agonists such as
   clonidine (Catapres), dosage range from 10 ug daily to 1.2 mg daily;
   clonidine TTS (Catapres TTS transdermal skin patch), dosage range from 0.1 mg daily to 0.3 mg daily;
   guanabenz (Wytensin), dosage range from 0.4 mg daily to 64 mg daily;
   guanfacine (Tenex), 0.1 mg daily to 3 mg daily; and
   methyldopa (Aldomet), dosage range from 25 mg daily to 2 gm daily;
peripherally acting adrenergic antagonists such as
   guanadrel (Hylorel), dosage range from 1 mg daily to 100 mg daily;
   guanethidine (Ismelin), dosage range from 1 mg daily to 150 mg daily;
   whole root Rauwolfia alkaloids (Raudixin), dosage range from 5 mg daily to 100 mg daily; and
   reserpine (Serpasil), dosage range from 10 ug daily to 0.25 mg daily;
α-adrenergic antagonists such as
   prazosin (Minipress, Pfizer Labs Division), dosage range from 0.1 mg daily to 20 mg daily;
   prazosin/polythiazide combination (Minizide, Pfizer Labs Division), dosage range from 0.1 mg prazosin and 50 ug polythiazide daily to 20 mg prazosin and 2 mg polythiazide daily;
   terazosin (Hytrin), dosage range from 0.1 mg daily to 20 mg daily;
   and doxazosin (Cardura), dosage range from 0.1 mg daily to 16 mg daily;
direct-acting vasodilators such as
   hydralazine (Apresoline), dosage range from 3 mg daily to 300 mg daily; and
   minoxidil (Loniten), 0.25 mg daily to 100 mg daily; and
(j) drugs for use in treatment of ischemic heart disease including nitrates such as
oral isosorbide dinitrate, dosage range from 2 mg daily to 240 mg daily; and
sustained-release trinitroglycerin, dosage range from 1 mg daily to 540 mg daily;
β-adrenergic antagonists such as
   acebutolol (Sectral), dosage range from 20 mg daily to 1.2 gm daily;
   atenolol (Tenormin), dosage range from 2.5 mg daily to 200 mg daily;

betaxolol (Kerlone), dosage range from 1 mg daily to 20 mg daily;

carteolol (Cartrol), dosage range from 0.25 mg daily to 10 mg daily;

labetalol (Normodyne), dosage range from 20 mg daily to 1.8 gm daily;

metoprolol (Lopressor), dosage range from 5 mg daily to 200 mg daily;

nadolol (Corgard), dosage range from 4 mg daily to 240 mg daily;

penbutolol (Levatol), dosage range from 2 mg daily to 80 mg daily;

pindolol (Visken), dosage range from 0.5 mg daily to 60 mg daily;

propranolol (Inderal or Inderal LA), dosage range from 4 mg daily to 320 mg daily;

timolol (Blocadren), dosage range from 1 mg daily to 60 mg daily; and bisoprolol (Zebeta, Lederle), dosage range from 0.5 mg daily to 10 mg daily;

and calcium channel antagonists such as diltiazem (Cardizem or Cardizem SR), dosage range from 10 mg daily to 360 mg daily;

verapamil (Calan or Calan SR), dosage range from 10 mg to 480 mg;

nifedipine (Procardia), dosage range from 3 mg daily to 180 mg daily;

nifedipine (Procardia XL), dosage range from 3 mg daily to 90 mg daily;

nicardipine (Cardene), dosage range from 6 mg daily to 120 mg daily;

isradipine (DynaCirc), dosage range from 0.5 mg daily to 20 mg daily;

amlodipine (Norvasc, Pfizer Labs Division), dosage range from 0.5 mg daily to 10 mg daily; and felodipine (Plendil, Merck & Co.), dosage range from 0.5 mg daily to 20 mg daily; and (k) ventricular antiarrhythmic drugs such as sotalol (Betapace, Berlex), dosage range from 30 mg daily to 320 mg daily;

mexilitene (Mexitil, Boehringer Ingelheim), dosage range from 60 mg daily to 1.2 gm daily;

propafenone (Rythmol, Knoll), dosage range from 45 mg daily to 900 mg daily;

quinidine (Quinaglute Dura-Tabs, Berlex), dosage range from 20 mg daily to 1.2 gm daily;

procainamide (Procan SR, Parke-Davis), dosage range from 200 mg daily to 5 gm daily;

pirmenol (Pimavar, Warner-Lambert), intravenous or oral dosage range from 25 mg daily to 500 mg daily.

Without further elaboration the foregoing will so fully illustrate my invention that others may, by applying current or future knowledge, adapt the same for use under various conditions of service.

I claim:

1. A method of treating the underlying biochemical symptoms of neurological diseases in a mammal, said method comprising a systemic administration of a composition consisting essentially of (a) at least one required primary agent administered orally to said mammal in a therapeutically effective amount in a dosage range of from about 15 mg/kg/day to about 450 mg/kg/day, said required primary agent being a pharmaceutically acceptable salt, free acid or pharmaceutically acceptable ester of the phenyl, cyclohexadiene, cyclohexene or cyclohexane carboxylic acid chemical structure of the formula

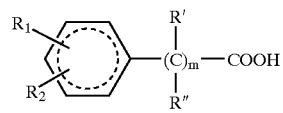

wherein $R_1$ is selected from the group consisting of $-NH_2$; ε-aminoalkyl having 1–10 carbons linear or branched and hydroxylated derivatives of this structure; $-NHC(=NH)NH_2$; $-(CH_2)_n NHC(=NH)NH_2$ wherein n is 1–10 hydrocarbons linear or branched and hydroxylated derivatives of this structure; $-C(=NH)NH_2$; $-(CH_2)_n-CH=NH(=NH)NH_2$ wherein n is 1–10 hydrocarbons linear or branched and hydroxylated derivatives of this structure; $-NHC(=NH)NHNH_2$; $-(CH_2)_n NHC(=NH)NHNH_2$ wherein n is 1–10 hydrocarbons linear or branched and hydroxylated derivatives of this structure; $-(CH_2)_n-CH=NC(=NH)NHNH_2$ wherein n is 1–10 hydrocarbons linear or branched and hydroxylated derivatives of this structure; $-NHNHC(=NH)NH_2$; $-(CH_2)_n NHNHC(=NH)NH_2$ wherein n is 1–10 hydrocarbons linear or branched and hydroxylated derivatives of this structure; and $-(CH_2)_n-CH=N-NHC(=NH)NH_2$ wherein n is 1–10 hydrocarbons linear or branched and hydroxylated derivatives of this structure;

$R_2$ is selected from the group consisting of H; $-NH_2$; $-OH$; $-O-CH_3$; $-OR'$ wherein R' is alkyl of 2–10 hydrocarbons linear or branched and hydroxylated derivatives of this structure; ε-aminoalkyl wherein the alkyl group is 1–10 hydrocarbons linear or branched and hydroxylated derivatives of this structure; $-SO_3H$; $-CH_3$; and $-(CH_2)_n CH_3$ wherein n is 1–10 hydrocarbons linear or branched and hydroxylated derivatives of this structure; and R' and R" are H, $-OH$ or $-CH_3$; and m is 0 or 1;

(b) optionally in combination with a therapeutically effective amount of one or more additional co-agent selected from the group consisting of non-absorbable polyamine carbonyl trapping substances, antioxidants, vitamins, metabolites at risk of depletion, sulfhydryl substance co-agents and co-agents which may facilitate glutathione activity; (c) optionally in combination with one or more co-agent medicament in an amount effective to treat the neurological disease; said composition furthermore optionally including (d) a pharmaceutically acceptable carrier suitable for the orally administered component thereof wherein the carrier is selected from the group consisting of carboxymethyl cellulose, microcrystalline cellulose, cellulose, starch, dicalcium phosphate, tricalcium phosphate, stearic acid, magnesium stearate, silica, soy flour, watercress, yeast, alfalfa, parseley, lecithin, rice bran, gum tragacanth, gum guar, gum agar, gum arabic, gum carrageenan, gum ghatti, gum karaya, locust bean gum, gum mastic, gum mesquite and gum xanthan, which may include all of the ingredients of said composition; and said composition furthermore optionally including (e) a pharmaceutically acceptable carrier suitable for systemic administration by the intravenous, intramuscular or subcutaneous route of one or more co-agent medicament.

2. The method of claim 1 for treating a human suffering from the symptomology of a neurodegenerative disease, wherein said disease is selected from the group consisting of hereditary motor and sensory neuropathies; diabetic polyneuropathy; Alzheimer's presenile dementia; Alzheimer's senile dementia; Down's syndrome; Parkinson's disease; amyotrophic lateral sclerosis; age-related atrophy of peripheral sensory and motor nerves; age-related atrophy of autonomic nerves resulting in symptoms of hypoperistalisis of the alimentary tract, hiatal hernia, partial food regurgitation, urinary incontinence, breathing insufficiency due to diaphram weakness or decreased autonomic sexual function; age-related atrophy of neurons of the central nervous system; age-onset pathophysiologically related changes in the kidney, optic lens and cardiovascular system, atherosclerosis and symptoms related thereto; alcoholic polyneuropathy; multiple sclerosis; olivopontocerebellar atrophy and Huntington's disease; said method comprising administering to said human a therapeutically effective amount of a composition of claim 1 sufficient to treat said human for said symptomology.

3. The method according to claim 2 wherein the disease is Alzheimer's senile dementia.

4. The method according to claim 2 wherein the disease is Alzheimer's presenile dementia.

5. The method according to claim 2 wherein the disease is a hereditary motor and sensory neuropathy.

6. The method according to claim 2 wherein the disease is Down's syndrome.

7. The method according to claim 2 wherein the disease is diabetic polyneuropathy.

8. The method according to claim 2 wherein the disease is Parkinson's disease.

9. The method according to claim 2 wherein the disease is amyotrophic lateral sclerosis.

10. The method according to claim 2 wherein the disease is age-related atrophy of peripheral sensory and motor nerves.

11. The method according to claim 2 wherein the disease is age-related atrophy of autonomic nerves resulting in symptoms of hypoperistalisis of the alimentary tract, hiatal hernia, partial food regurgitation, urinary incontinence, breathing insufficiency due to diaphram weakness or decreased autonomic sexual function.

12. The method according to claim 2 wherein the disease is age-related atrophy of neurons of the central nervous system.

13. The method according to claim 2 wherein the disease is age-onset pathophysiologically related changes in the kidney, optic lens and cardiovascular system.

14. The method according to claim 2 wherein the disease is atherosclerosis.

15. The method according to claim 2 wherein the disease is alcoholic polyneuropathy.

16. The method according to claim 2 wherein the disease is multiple sclerosis.

17. The method according to claim 2 wherein the disease is olivopontocerebellar atrophy.

18. The method according to claim 2 wherein the disease is Huntington's disease.

19. The method of claim 1 for treatment of a mammal, wherein said mammal is a human, said method comprising administering to said human a therapeutically effective amount of an optional non-absorbable polyamine carbonyl trapping substance co-agent sufficient to treat said human wherein said co-agent is selected from the group consisting of:

a. naturally occurring polysaccharides having β-1,2, β-1,3, β-1,4 and/or β-1,6 linkages containing aminosugars;

b. deacetylated. naturally occurring polysaccharides, having at least one N-acetylated residue;

c. chemically aminated polysaccharides selected from the group consisting of:
   aminodeoxy polysaccharides; aminoalkyl-, amino (hydroxyalkyl)-, aminoalkyl-ether-, and amino (hydroxyalkyl)-ether-derivatives of cellulose, chitin and other naturally occurring non-digestible carbohydrates selected from the group consisting of
   $H_2N-(CH_2)_n$-[carbohydrate] where n=1–10;
   $H_2N-(CH_2)_n-CHOH-(CH_2)_n$-[carbohydrate], where m=0–10 and n=0–10;
   $H_2N-(CH_2)_n-O$-[carbohydrate] where n=1–10;
   $H_2N-(CH_2)_n-CHOH-(CH_2)_n-O$-[carbohydrate] where m=0–10 and n=0–10;
   aminobenzyl-derivatives of cellulose, chitin or other naturally occurring non-digestible carbohydrates selected from the group consisting of
   $H_2N-C_6H_4-(CH_2)_n$-[carbohydrate],
   $H_2N-CH_2-C_6H_4-(CH_2)_n$-[carbohydrate],
   $H_2N-C_6H_4-(CH_2)_n-O$-[carbohydrate] where n=0–10, and
   $H_2N-C_6H_4-(CH_2)_n-CHOH-(CH_2)_n-O$-[carbohydrate] where m=0–10 and n=0–10, including p-, o- and m-benzene ring amino- and aminomethyl-isomers, and alkyl group isomers;
   guanidine and aminoguanidine derivatives of cellulose, chitin or other naturally occurring non-absorbable carbohydrates selected from the group consisting of:
   $H_2N-C(=NH)$-[carbohydrate];
   $H_2N-C(=NH)-(CH_2)_n$-[carbohydrate], where n=1–10, including hydrocarbon isomers and hydroxylated derivatives thereof;
   $H_2N-C(=NH)-O-(CH_2)_n$-[carbohydrate], where n=1–10, including hydrocarbon isomers, ether linkage isomers and hydroxylated derivatives thereof;
   $H_2N-C(=NH)-NH$-[carbohydrate];
   $H_2N-C(=NH)-NH-(CH_2)_n$-[carbohydrate], where n=1–10, including hydrocarbon isomers and hydroxylated derivatives thereof;
   $H_2N-C(=NH)-NH-(CH_2)_n-O$-[carbohydrate], where n=1–10, including hydrocarbon isomers, ether linkage isomers and hydroxylated derivatives thereof;
   $H_2N-C(=NH)-N=CH-(CH_2)_n$-[carbohydrate], where n=1–10, including hydrocarbon isomers and hydroxylated derivatives thereof;
   $H_2N-C(=NH)-N=CH-(CH_2)_n-O$-[carbohydrate], where n=1–10, including hydrocarbon isomers and hydroxylated derivatives thereof;
   $H_2N-NHC(=NH)-NH$-[carbohydrate];
   $H_2N-NHC(=NH)-NH-(CH_2)_n$-[carbohydrate], where n=1–10, including hydrocarbon isomers and hydroxylated derivatives thereof;
   $H_2N-NHC(=NH)-NH-(CH_2)_n-O$-[carbohydrate], where n=1–10, including hydrocarbon isomers, ether linkage isomers and hydroxylated derivatives thereof;
   $H_2N-NHC(=NH)-N=CH-(CH_2)_n$-[carbohydrate], where n=1–10, including hydrocarbon isomers and hydroxylated derivatives thereof;
   $H_2N-NHC(=NH)-N=CH-(C_2)_n-O$-[carbohydrate], where n=1–10, including hydrocarbon isomers, ether linkage isomers and hydroxylated derivatives thereof;

H₂N—C(=NH)—NH—NH-[carbohydrate];

H₂N—C(=NH)—NH—NH—(CH₂)ₙ-[carbohydrate], where n=1–10, including hydrocarbon isomers and hydroxylated derivatives thereof;

H₂N—C(=NH)—NH—NH—(CH₂)ₙ—O-[carbohydrate], where n=1–10, including hydrocarbon isomers, ether linkage isomers and hydroxylated derivatives thereof;

H₂N—C(=NH)—NH—N=CH—(CH₂)ₙ-[carbohydrate], where n=1–10, including hydrocarbon isomers and hydroxylated derivatives thereof;

H₂N—C(=NH)—NH—N=CH—(CH₂)ₙ—O-[carbohydrate], where n=1–10, including hydrocarbon isomers, ether linkage isomers and hydroxylated derivatives thereof;

d. primary amine, aminoguanidine and guanidine derivatives of sucrose polyesters having one or more carbonyl trapping functional group per molecule wherein each carbonyl trapping functional group is in the ω-, ω-1 or other isomeric position within the fatty acyl chains, wherein each fatty acyl chain may have from 3 to 26 carbons, from one to five nitrogen functional groups and from one to 24 hydroxyl groups;

e. synthetic polysaccharides consisting partly or entirely of aminosugars bound by β-1,2, β-1,3, β-1,4 and/or β-1,6 linkages;

f. mixed polysaccharide polymeric derivatives wherein primary amine, aminoalkyl (one to ten carbons per alkyl group), aminohydroxyalkyl (one to ten carbons per alkyl group and one to ten hydroxyl groups per alkyl group), aminoguanidine, aminoguanidinylalkyl (one to ten carbons per alkyl group), aminoalkylguanidinyl (one to ten carbons per alkyl group), guanidine, aminobenzene and/or aminoalkylbenzene (one to ten carbons per alkyl group) functional groups are covalently attached to matrices; and g. non-polysaccharide polymeric derivatives wherein primary amine, aminoalkyl (one to ten carbons per alkyl group), aminohydroxyalkyl (one to ten carbons per alkyl group and one to ten hydroxyl groups per alkyl group), aminoguanidine, aminoguanidinylalkyl (one to ten carbons per alkyl group), aminoalkylguanidinyl (one to ten carbons per alkyl group), guanidine, aminobenzene and/or aminoalkylbenzene (one to ten carbons per alkyl group) functional groups are covalently attached to a synthetic non-digestible polymer selected from the group consisting of polystyrene, styrene-divinylbenzene copolymer, polyvinyl alcohol and crosslinked derivatives thereof, and wherein hydrocarbon spacer groups are selected from alkene and alkyl groups.

20. The method of claim 1 wherein said optional non-absorbable polyamine carbonyl trapping substance co-agent is in a micro-fibrillated form or microcrystalline form having enhanced surface area, increased porosity, increased water retention capacity and enhanced chemical accessibility.

21. The method of claim 1 wherein the antioxidant is selected from the group consisting of α-tocopherol, β-tocopherol, γ-tocopherol, δ-tocopherol, ε-tocopherol, ζ₁-tocopherol, ζ₂-tocopherol, η-tocopherol, pharmaceutically acceptable tocopherol derivatives, citric acid, coenzyme Qₙ where n=1–12, glutathione, butylated hydroxytoluene, butylated hydroxyanisole, propyl gallate, dodecylgallate, tert-butylhydroquinone, dihydrolipoic acid, prostaglandin B₁ oligomers, 2-aminomethyl-4-tert-butyl-6-iodophenol, 2-aminomethyl-4-tert-butyl-6-propionylphenol, 2,6-di-tert-butyl-4-[2'-thenoyl]phenol, N,N'-diphenyl-p-phenylenediamine, ethoxyquin, probucol, ebselen, 5-[[3,5-bis(1,1-dimethylethyl)-4-hydroxyphenyl]methylene]-3-(dimethylamino)-4-thiazolidinone 5-[[3,5-bis(1,1-dimethylethyl)-4-hydroxyphenyl]methylene]-3-(methylamino)-4-thiazolidinone, D-myoinositol-1.2.6-trisphosphate, nordihydroguaiaretic acid, deferoxamine mesylate, tirilazad mesylate, derivative of tirilazad in which the steroid portion of the chemical structure has been replaced with the tetramethyl chroman portion of d-α-tocopherol, trimetazidine, N,N'-dimethylthiourea, 2-(2-hydroxy-4-methylphenyl)aminothiazole hydrochloride, 2-L-oxothiazolidine, α-lipoic acid, sodium α-lipoate, ethylenediamine α-lipoate, selenium, pharmaceutically acceptable salts of selenium, a seleno-containing amino acid, zinc, pharmaceutically acceptable salts of zinc, parthenolide, lycopene, daidzin, genistein, quercetin, morin, curcumin, apigenin, sesamol, chlorogenic acid, fisetin, ellagic acid, quillaia saponin, capsaicin, ginsenoside, silymarin, kaempferol, ginkgetin, bilobetin, isoginkgetin, isorhamnetin, herbimycin, rutin, bromelain, levendustin A and erbstatin.

22. The method of claim 1 wherein the vitamin is selected from the group consisting of retinol, vitamin A aldehyde, vitamin A acid, retinyl acetate, vitamin B₁, thiamine propyl disulfide, thiamine disulfide, thiamine disulfide O,O-diisobutyrate, thiamine disulfide hydrochloride, thiamine disulfide phosphate, thiamine mononitrate, thiamine 1,5-salt, thiamine phosphoric acid ester chloride, thiamine phosphoric acid ester phosphate salt, thiamine triphosphoric acid ester, vitamin B₂, riboflavin tetrabutyrate, riboflavine 5'-phosphate ester monosodium salt, pantothenic acid, pantothenic acid sodium salt, pantothenic acid calcium salt, vitamin B₆, pyridoxal, pyridoxal HCl, pyridoxal 5-phosphate, pyridoxal 5-phosphate calcium salt, pyridoxamine, pyridoxamine dihydrochloride, pyridoxamine phosphate, vitamin B₁₂, methyl vitamin B₁₂, vitamin D₂, vitamin D₃, vitamin D₄, vitamin H, vitamin K₁, diacetyl dihydro vitamin K₁, vitamin K₁ oxide, vitamin(s) K₂, vitamin K₂₍₃₅₎, vitamin K₂₍₃₅₎ dihydrodiacetate, vitamin K₂₍₃₀₎, vitamin K₂₍₃₀₎ dihydrodiacetate, vitamin K₅, vitamin K₅ hydrochloride, N-acetyl vitamin K₅, vitamin K₆, vitamin K₆ dihydrochloride, vitamin K₇, vitamin K₇ hydrochloride, vitamin K-S(II), vitamin L₁, vitamin L₂, vitamin U, methylmethioninesulfonium bromide, α-carotene, β-carotene, γ-carotine, ω-carotene, Ψ-,Ψ-carotene, 7,7',8,8',11,12-hexahydro-Ψ-,Ψ-carotene, L-carnitine, acetyl-L-carnitine, folic acid, folinic acid, folinic acid calcium salt pentahydrate, niacinamide, nicotinic acid, nicotinic acid sodium salt sesquihydrate and nicotinic acid monoethanolamine salt.

23. The method of claim 1 wherein the co-agent which facilitates glutathione biological activity is selected from the group consisting of N-acetylcysteine, oxothiazolidinecarboxylate, timonacic acid, cysteamine and lipoamide derivatives.

24. The method of claim 1 wherein the metabolite at risk of depletion is selected from the group consisting of glycine and pharmaceutically acceptable salts thereof.

25. The method of claim 1 wherein the sulfhydryl substance co-agent is a sulfhydryl containing substance or derivative thereof selected from the group consisting of cysteine, homocysteine and methionine.

26. The method of claim 1 wherein the co-agent selected from the group consisting of non-absorbable polyamine carbonyl trapping substances, antioxidants, vitamins, metabolites at risk of depletion, sulfhydryl substance co-agents and co-agents which may facilitate glutathione activity is administered orally.

27. The method of claim 1 wherein the co-agent selected from the group consisting of antioxidants, vitamins, metabolites at risk of depletion, sulfhydryl substance co-agents and co-agents which may facilitate glutathione activity is administered intravenously, intramuscularly or subcutaneously.

28. A method of treating the underlying biochemical symptoms of neurological diseases in a human comprising the method of claim 1 and the added administration of a co-agent medicament effective to treat the disease or a symptom thereof.

29. A method of treating the underlying biochemical symptoms of veterinary neurological diseases in a mammal, said method comprising administering to the mammal a therapeutically effective amount of at least one orally administered required primary agent of claim 1 wherein the orally administered required primary agent is in a dosage in the range of 15 mg/kg daily to 450 mg/kg daily and may be administered for extended periods of time.

30. The method of claim 29 wherein the mammal is also treated with a therapeutically effective amount of at least one optional co-agent from the group consisting of non-absorbable polyamine carbonyl trapping substances, antioxidants, vitamins, metabolites at risk of depletion, sulfhydryl substance co-agents and co-agents which may facilitate glutathione activity as defined in claim 1.

31. The method according to claim 29, said method additionally comprising the added administration of a co-agent medicament effective to treat the disease or a symptom thereof.

32. The method of claim 1 wherein the category (c) medicament co-agent effective to treat the disease or a symptom thereof is administered orally.

33. The method of claim 1 wherein the category (c) medicament co-agent effective to treat the disease or a symptom thereof is administered intravenously, intramuscularly or sub-cutaneously.

* * * * *